United States Patent
Lee et al.

(10) Patent No.: US 11,972,510 B2
(45) Date of Patent: Apr. 30, 2024

(54) METHOD FOR GENERATING TOMOGRAPHIC IMAGE AND X-RAY IMAGING APPARATUS ACCORDING TO SAME

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jongha Lee, Suwon-si (KR); Hyeongseok Kim, Daejeon-si (KR); Seungryong Cho, Daejeon-si (KR); Namuk Kim, Suwon-si (KR); Jonghwan Min, Suwon-si (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 635 days.

(21) Appl. No.: 17/251,065

(22) PCT Filed: Jun. 10, 2019

(86) PCT No.: PCT/KR2019/006939
§ 371 (c)(1),
(2) Date: Dec. 10, 2020

(87) PCT Pub. No.: WO2019/240444
PCT Pub. Date: Dec. 19, 2019

(65) Prior Publication Data
US 2021/0125384 A1    Apr. 29, 2021

(30) Foreign Application Priority Data
Jun. 11, 2018 (KR) .................. 10-2018-0067037

(51) Int. Cl.
*G06T 11/00* (2006.01)

(52) U.S. Cl.
CPC .......... *G06T 11/005* (2013.01); *G06T 11/006* (2013.01); *G06T 2210/41* (2013.01); *G06T 2211/421* (2013.01)

(58) Field of Classification Search
CPC ..... A61B 6/032; A61B 6/5205; A61B 6/5258; A61B 6/482; A61B 6/025; A61B 6/469;
(Continued)

(56) References Cited

U.S. PATENT DOCUMENTS

| | | | |
|---|---|---|---|
| 8,483,463 B2 * | 7/2013 | Chen | G06T 11/006 382/131 |
| 9,087,404 B2 | 7/2015 | Hansis et al. | |

(Continued)

FOREIGN PATENT DOCUMENTS

| | | |
|---|---|---|
| CN | 101268950 A | 9/2008 |
| EP | 3404615 A1 * | 11/2018 |

(Continued)

OTHER PUBLICATIONS

Communication dated Oct. 5, 2022, issued by the Korean Intellectual Property Office in Korean Patent Application No. 10-2018-0067037.

(Continued)

*Primary Examiner* — Ian L Lemieux
*Assistant Examiner* — Woo C Rhim
(74) *Attorney, Agent, or Firm* — Sughrue Mion, PLLC

(57) ABSTRACT

An embodiment of the present disclosure provides a method of generating a tomography image and an X-ray imaging apparatus operating according to the method, whereby when a material with a high X-ray attenuation rate is inserted into an object, an image quality may be improved by reducing ripple artifacts and/or undershoot artifacts that may occur in (Continued)

a tomography image that is a captured X-ray image of the object.

16 Claims, 19 Drawing Sheets

(58) Field of Classification Search
CPC ....... A61B 6/00; G06T 11/005; G06T 11/006; G06T 11/008; G06T 2207/10081; G06T 2211/424; G06T 2211/421; G06T 11/003; G06T 2207/10116; G06T 2211/416; G06T 2210/41; G06T 2211/436; G06T 2207/10072; G01N 23/046; G01N 2223/419; G01N 2223/1016
See application file for complete search history.

(56) References Cited

U.S. PATENT DOCUMENTS

| | | | |
|---|---|---|---|
| 9,486,178 B2 | 11/2016 | Sakimoto et al. | |
| 9,741,127 B1 | 8/2017 | Watanabe et al. | |
| 9,892,527 B2 | 2/2018 | Ye et al. | |
| 10,512,437 B2 | 12/2019 | Lee et al. | |
| 2005/0100127 A1* | 5/2005 | Zhao | A61B 6/4085 378/19 |
| 2006/0198491 A1* | 9/2006 | Taguchi | A61B 6/027 378/15 |
| 2010/0232663 A1* | 9/2010 | Bontus | A61B 6/027 382/131 |
| 2011/0013817 A1* | 1/2011 | Medow | G06T 11/006 382/131 |
| 2013/0077847 A1* | 3/2013 | Hansis | G06T 11/006 382/131 |
| 2013/0243152 A1* | 9/2013 | Hagiwara | G06T 11/005 378/19 |
| 2014/0369463 A1* | 12/2014 | Thibault | A61B 6/032 378/19 |
| 2015/0036788 A1* | 2/2015 | Baba | A61B 6/027 378/4 |
| 2015/0036902 A1* | 2/2015 | Zamyatin | G06T 7/0012 382/131 |
| 2015/0085972 A1* | 3/2015 | Choi | G06T 11/006 378/8 |
| 2015/0243045 A1* | 8/2015 | Ra | G06T 7/248 382/131 |
| 2015/0243070 A1* | 8/2015 | Ra | A61B 6/5217 382/131 |
| 2015/0302615 A1* | 10/2015 | Fukuda | A61B 6/032 378/19 |
| 2016/0015350 A1* | 1/2016 | Chang | A61B 6/032 250/362 |
| 2016/0054239 A1 | 2/2016 | Schlecht et al. | |
| 2016/0171726 A1* | 6/2016 | Nam | G06T 11/006 382/131 |
| 2016/0206268 A1* | 7/2016 | Fukuda | A61B 6/5205 |
| 2016/0206269 A1* | 7/2016 | Jung | A61B 6/4241 |
| 2016/0225170 A1* | 8/2016 | Rifu | G06T 11/005 |
| 2016/0242720 A1* | 8/2016 | Ida | A61B 6/032 |
| 2016/0253818 A1* | 9/2016 | Tang | G06T 5/50 382/131 |
| 2016/0256127 A1* | 9/2016 | Lee | A61B 6/5264 |
| 2016/0292849 A1* | 10/2016 | Lee | G06T 5/001 |
| 2016/0300370 A1* | 10/2016 | Yoo | G06T 11/005 |
| 2016/0367212 A1 | 12/2016 | Tang et al. | |
| 2017/0000451 A1 | 1/2017 | Aspelund et al. | |
| 2017/0042494 A1* | 2/2017 | Kim | G06T 11/006 |
| 2017/0055932 A1* | 3/2017 | Lee | A61B 6/5264 |
| 2017/0209112 A1* | 7/2017 | Yi | A61B 6/032 |
| 2017/0258432 A1* | 9/2017 | Choi | A61B 6/563 |
| 2017/0303868 A1* | 10/2017 | Lee | G06T 11/006 |
| 2017/0316588 A1* | 11/2017 | Homann | G06T 11/008 |
| 2017/0340304 A1* | 11/2017 | Qiulin | A61B 6/5205 |
| 2018/0055460 A1 | 3/2018 | Matthews | |
| 2018/0096476 A1* | 4/2018 | Tang | G06T 11/005 |
| 2018/0158216 A1* | 6/2018 | Cao | G06T 11/006 |
| 2018/0158218 A1* | 6/2018 | Yoon | A61B 6/032 |
| 2020/0143521 A1* | 5/2020 | Wang | G06T 7/11 |
| 2022/0292646 A1* | 9/2022 | Wang | G06T 11/006 |

FOREIGN PATENT DOCUMENTS

| | | |
|---|---|---|
| JP | 2010-240257 A | 10/2010 |
| JP | 5899208 B2 | 4/2016 |
| JP | 2017-6640 A | 1/2017 |
| JP | 2018-33966 A | 3/2018 |
| KR | 10-1101887 B1 | 1/2012 |
| KR | 10-2016-0057935 A | 5/2016 |
| KR | 10-1636207 B1 | 7/2016 |
| KR | 10-2016-0091377 A | 8/2016 |
| KR | 10-2018-0057902 A | 5/2018 |
| WO | WO-2017014406 A1 * | 1/2017 ............ A61B 6/00 |

OTHER PUBLICATIONS

Zhang, Zhaoxia et al., "Metal artifact reduction in tomosynthesis imaging" Proc. SPIE 9412, Medical Imaging 2015: Physics of Medical Imaging, 94125A, Mar. 18, 2015; doi:10.1117/12.2080923. (9 pages total).

International Search Report and Written Opinion dated Sep. 16, 2019 by the International Searching Authority in counterpart International Patent Application No. PCT/KR2019/006939. (PCT/ISA/210/220/237).

* cited by examiner

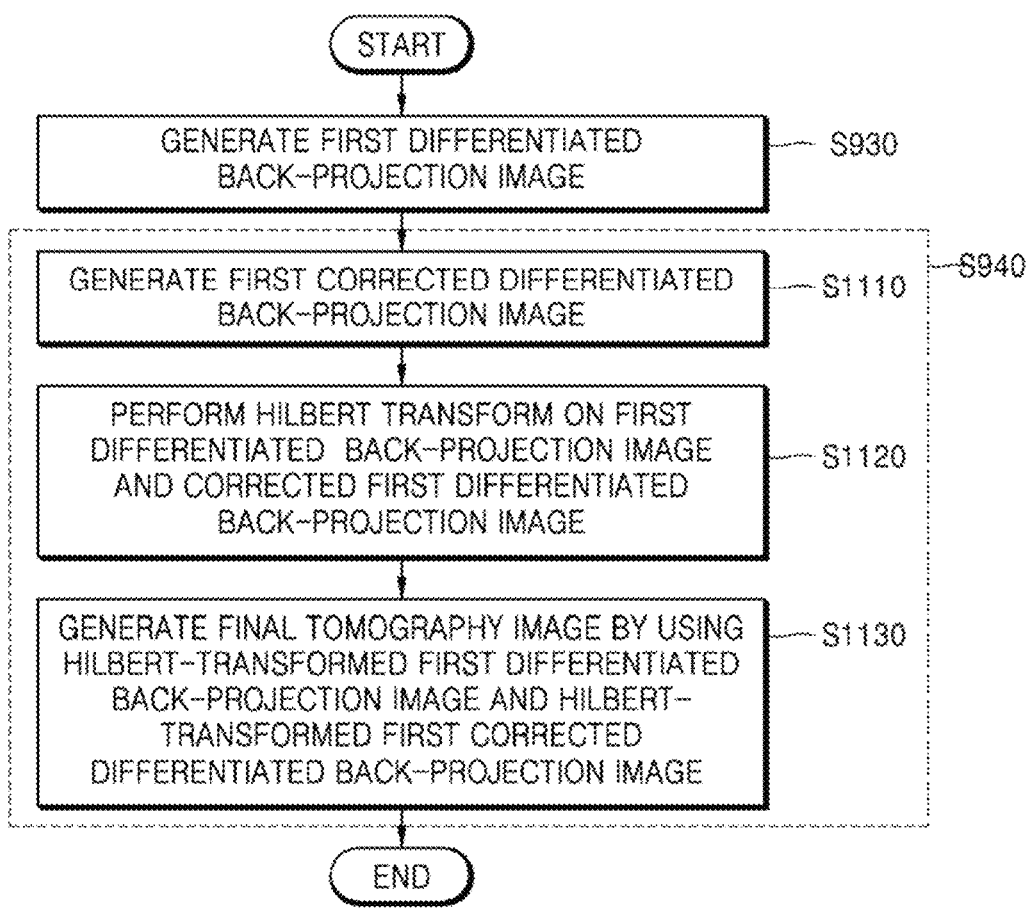

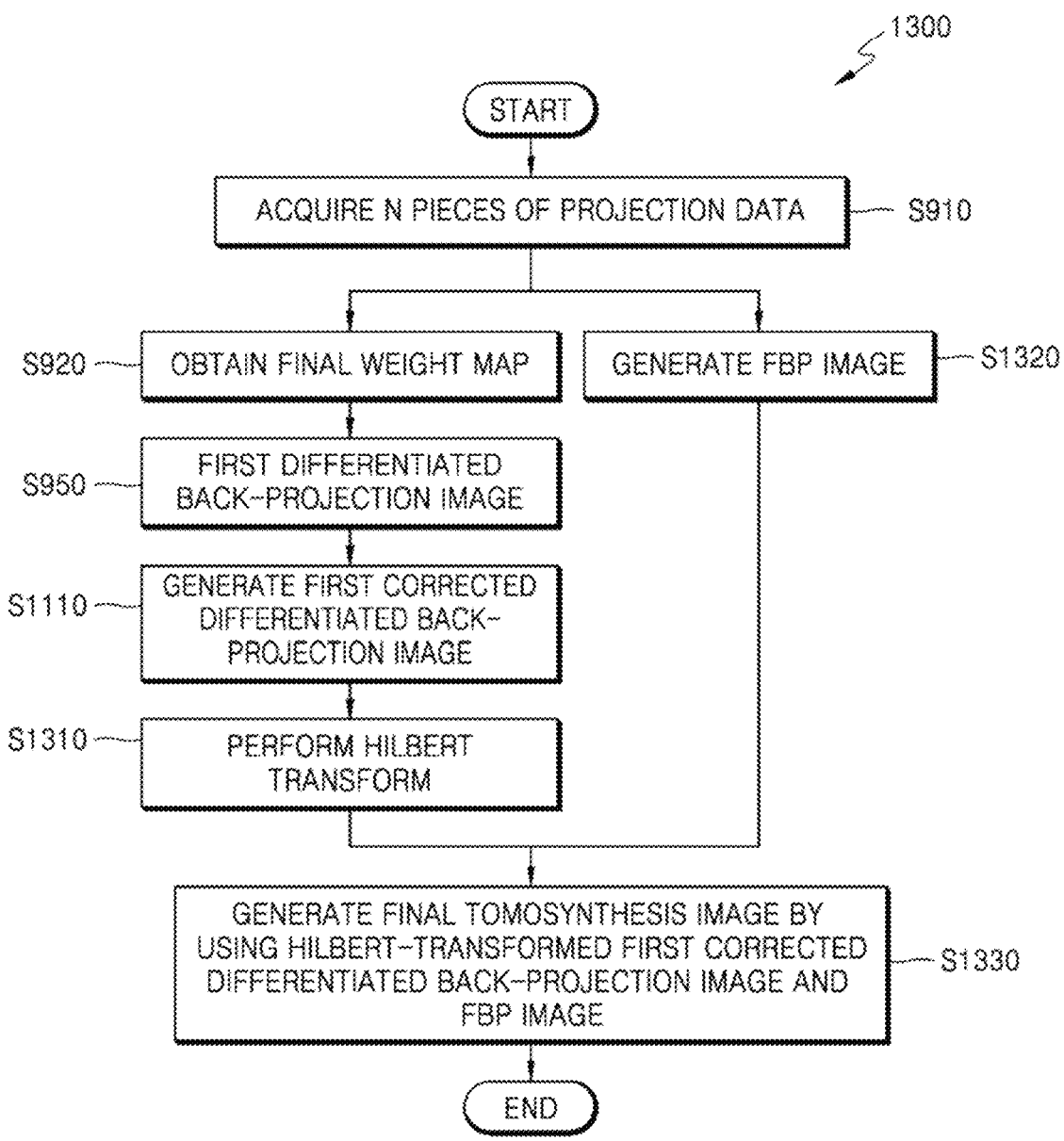

METHOD FOR GENERATING TOMOGRAPHIC IMAGE AND X-RAY IMAGING APPARATUS ACCORDING TO SAME

TECHNICAL FIELD

Embodiments of the present disclosure relate to a method of generating a tomography image and an X-ray imaging apparatus operating according to the method, and more particularly, to a tomography image generation method for reconstructing a tomography image by using data acquired by emitting X-rays onto an object and an X-ray imaging apparatus operating according to the tomography image generation method.

BACKGROUND ART

Medical imaging technology using X-rays is a technology for generating images of the inside of a human body by using the principle that a degree of attenuation varies according to an attenuation coefficient of a material constituting the object as the X-rays pass through the object.

Because X-rays are capable of visualizing an anatomical structure of a human body, the X-rays are used to identify pathological phenomena, diseases, or abnormal anatomical structures inside the human body. However, use of X-ray technology has a limitation in that it is difficult to provide three-dimensional (3D) information about an internal structure of the human body. In other words, because an existing X-ray image is only a two-dimensional (2D) image obtained with a film or an image sensor, use of such X-ray images in a medical field lacks 3D depth perception or a sense of reality during examination of the inside of the human body. Furthermore, because only a 2D image is obtained, use of such X-ray images have a problem that it is difficult to identify an internal structure of an object in a depth direction. Thus, in recent years, research has been conducted to extract 3D information about the inside of a patient's body by using a relatively easy-to-use method while limiting patient's exposure to radiation.

A tomosynthesis image reconstruction method is a technology for generating a 3D medical image via X-ray imaging. The tomosynthesis image reconstruction method may be called a digital tomosynthesis (DT) technology or a tomosynthesis technology. A technology for generating a 3D medical image via X-ray imaging will be hereinafter referred to as a 'tomosynthesis technology'.

A tomosynthesis technology is a technology for acquiring projection data within a limited angular range by using X-rays and reconstructing a tomosynthesis image from the acquired projection data, and an image reconstruction method based on analytic or iterative technique may be used in tomosynthesis image reconstruction In detail, a tomosynthesis image may be reconstructed using a back-projection filtration (BPF) method. A tomosynthesis image may be used to examine various body parts of a patient, such as the breast, chest, and joints.

In detail, a tomosynthesis technology is used to reconstruct an image in a manner similar to computed tomography (CT). An image reconstruction method based on an iterative technique may increase image quality but has drawbacks in that the method requires a long reconstruction time and a reconstructed image is highly dependent on image reconstruction parameters. Thus, an image reconstruction method based on an analytic technique is being widely used for commercial applications.

While the tomosynthesis technology is capable of obtaining a tomography image of an object in a human body, it has a problem in that a resolution in a depth direction is degraded due to image reconstruction based on limited data. Another problem is that severe artifacts occur when an artificial material, such as a metallic material, which is not a natural material constituting the human body, is inserted into the object.

Accordingly, there is a need for a method of generating a tomography image and an X-ray imaging apparatus operating according to the method, which are capable of reconstructing an image clearly showing an object by improving image quality.

DESCRIPTION OF EMBODIMENTS

Technical Problem

Provided are a method of generating a tomography image and an X-ray imaging apparatus operating according to the method, which are capable of reducing artifacts in a reconstructed tomography image.

In detail, provided are a method of generating a tomography image and an X-ray imaging apparatus operating according to the method, whereby when an object including a material with a high X-ray attenuation rate compared to its surrounding region is imaged, image quality may be improved by reducing ripple artifacts or undershoot artifacts that appear as an afterimage of the material.

Technical Solution to Problem

When an artificial material, such as a metallic material, which is not a natural material constituting a human body, is inserted into an object, artifacts caused by such an artificial material may be reduced.

Advantageous Effects of Disclosure

A method of generating a tomography image and an X-ray imaging apparatus operating according to the method according to embodiments of the present disclosure are capable of reducing artifacts in a reconstructed tomography image.

In detail, when a material having a large attenuation coefficient is inserted into an object, the method of generating a tomography image and the X-ray imaging apparatus operating according to the method according to the embodiments of the present disclosure are capable of improving image quality by reducing out-of-plane artifacts such as ripple artifacts or undershoot artifacts that may occur in a tomography image that is a captured X-ray image of the object.

In detail, when a metallic material having a large attenuation coefficient is inserted into the object, the method of generating a tomography image and the X-ray imaging apparatus operating according to the method according to the embodiments of the present disclosure are capable of improving image quality by reducing out-of-plane artifacts caused when a metallic material is imaged in a region in a tomography image other than a region where the metallic material needs to be imaged.

BRIEF DESCRIPTION OF DRAWINGS

FIG. 11 is a flowchart illustrating in detail operations performed to obtain a tomography image, according to an embodiment of the present disclosure.

FIG. 13 is a flowchart of a tomography image generation method, according to another embodiment of the present disclosure.

BEST MODE

Figure 1:
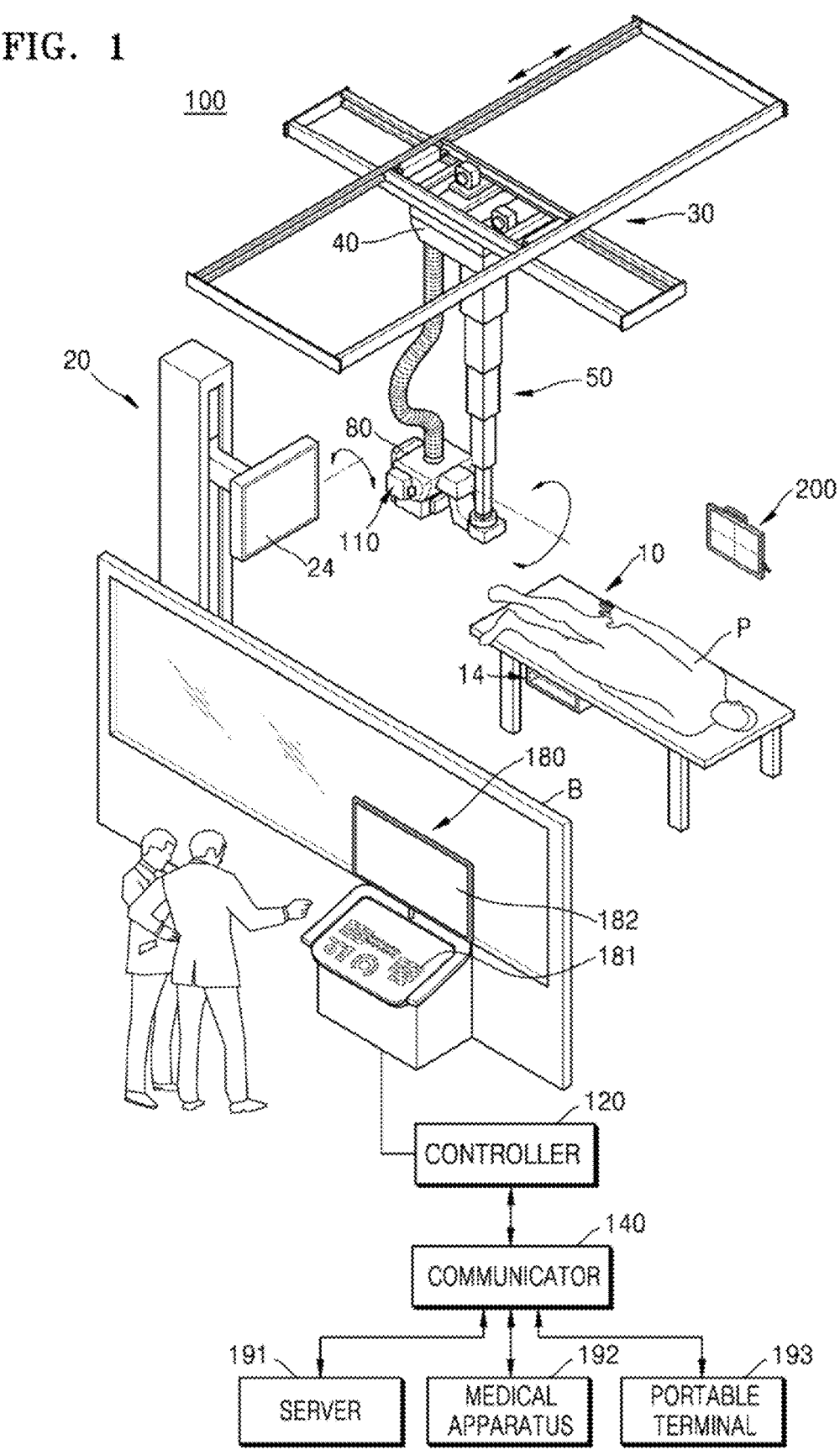
FIG. 1 is an external view illustrating a configuration of an X-ray apparatus according to an embodiment wherein the X-ray apparatus is a fixed X-ray apparatus.

According to an embodiment of the disclosure, a method of generating a tomography image includes: acquiring N pieces of projection data respectively corresponding to N views included in a first angular range; obtaining, based on M pieces of projection data respectively corresponding to M views among the N views, a final weight map applied when the N pieces of projection data are back-projected; and generating a final tomography image showing an object by using the final weight map and the N pieces of projection data.

The M views may be views extracted at a predetermined interval from among the N views included in the first angular range, and M may have a value less than or equal to N.

The predetermined interval may be an equal angular interval.

The method may further include generating a first image by correcting, based on the final weight map, N edge images respectively representing edge information in the N pieces of projection data and then back-projecting the corrected N edge images, and the generating of the final tomography image may include generating the final tomography image by using the first image The generating of the final tomography image may include: generating a first corrected image by correcting a pixel value of a region corresponding to a material having a high X-ray attenuation rate compared to its surrounding region included in the first image; and generating the final tomography image by using the first image and the first corrected image.

The material having a high X-ray attenuation rate compared to the surrounding region may be a material made of metal and may be at least one of a material inserted into a human body, bone, or a calcareous material.

The generating of the first corrected image may include generating a first corrected differentiated back-projection image by correcting, based on a pixel value of the first image, a pixel value of an outlier region in which the pixel value is greater than or equal to a predetermined threshold value or exceeds the predetermined threshold value.

The generating of the first image may include generating a first differentiated back-projection image that is the first image by correcting, based on the final weight map, N differentiated images obtained by respectively differentiating the N pieces of projection data and then back-projecting the corrected N differentiated images.

The generating of the final tomography image may include: generating a first corrected image by correcting a pixel value of a region corresponding to a material having a high X-ray attenuation rate compared to its surrounding region included in the first image; and generating the final tomography image by performing frequency modulation transformations respectively on the first image and the first corrected image and blending a frequency modulation-transformed first image with a frequency modulation-transformed first corrected image.

The frequency modulation transformation may be Hilbert transform.

The blending may include selectively capturing one of the Hilbert-transformed first image and the Hilbert-transformed first corrected image having larger pixel values.

The acquiring of the N pieces of projection data may include acquiring the N pieces of projection data via X-ray imaging in an X-ray apparatus by emitting X-rays toward the object while moving an X-ray radiation device over a first angular range and detecting X-rays that have passed through the object.

The acquiring of the N pieces of projection data may include acquiring the N pieces of tomography data from a computed tomography (CT) system or a tomosynthesis system.

The method of generating a tomography image may further include: generating a first image by correcting, based on the final weight map, N edge images generated by respectively performing edge enhancement for edge information in the N pieces of projection data and then back-projecting the corrected N edge images; generating a first corrected image by correcting a pixel value of a region corresponding to a material having a high X-ray attenuation rate compared to its surrounding region included in the first image; generating a frequency modulation-transformed first corrected image by performing frequency modulation transformation on the first corrected image; and generating a filtered back-projection image by performing filtered back-projection on the N pieces of projection data. The generating of the final tomography image may include generating the final tomography image by blending the frequency modulation-transformed first corrected image with the filtered back-projection image.

According to another embodiment of the disclosure, an X-ray imaging apparatus includes: a memory storing N pieces of projection data (a projection data set) respectively corresponding to N views included in a first angular range; and a controller storing one or more instructions and including at least one processor configured to perform the stored one or more instructions to: obtain, based on M pieces of projection data respectively corresponding to M views among the N views, a final weight map applied when the N pieces of projection data are back-projected; and generate a final tomography image showing an object by using the final weight map and the N pieces of projection data.

The M views may be views extracted at a predetermined interval from among the N views included in the first angular range, and the M may have a value less than or equal to the N.

The processor may be further configured to generate a first image by correcting, based on the final weight map, N edge images obtained by respectively performing enhancement of edge information in the N pieces of projection data and then back-projecting the corrected N edge images and generate the final tomography image by using the final weight map and the first image.

The processor may be further configured to generate a first corrected image by correcting a pixel value of a region corresponding to a material having a high X-ray attenuation rate compared to its surrounding region included in the first image and generate the final tomography image by using the first image and the first corrected image.

The processor may be further configured to generate a first corrected differentiated back-projection image by correcting, based on a pixel value of the first image, a pixel value of an outlier region in which the pixel value is greater than or equal to a predetermined threshold value or exceeds the predetermined threshold value.

The processor may be further configured to generate a first corrected image by correcting a pixel value of a region corresponding to a material having a high X-ray attenuation rate compared to its surrounding region included in the first image and generate the final tomography image by performing frequency modulation transformations respectively on the first image and the first corrected image and blending a frequency modulation-transformed first image with a frequency modulation-transformed first corrected image.

The X-ray imaging apparatus according to the embodiment of the disclosure may further include a data acquisition unit configured to acquire the N pieces of projection data via X-ray imaging by emitting X-rays toward the object while moving an X-ray radiation device over the first angular range and detecting X-rays that have passed through the object.

According to another embodiment of the present disclosure, a method of generating a tomography image includes: acquiring N pieces of projection data respectively corresponding to N views included in a first angular range; generating a first image by back-projecting N edge images respectively representing edge information in the N pieces of projection data; generating a first corrected image by correcting a pixel value of a region corresponding to a material having a high X-ray attenuation rate compared to its surrounding region included in the first image; generating a frequency modulation-transformed first corrected image by performing frequency modulation transformation on the first corrected image; generating a filtered back-projection image by performing filtered back-projection on the N pieces of projection data; and generating a final tomography image by blending the frequency modulation-transformed first corrected image with the filtered back-projection image.

The generating of the first corrected image may include generating a first corrected differentiated back-projection image by correcting, based on a pixel value of the first image, a pixel value of an outlier region in which the pixel value is greater than or equal to a predetermined threshold value or exceeds the predetermined threshold value.

The frequency modulation transformation may be Hilbert transform.

The method may further include obtaining, based on M pieces of projection data respectively corresponding to M views among the N views, a final weight map applied when the N pieces of projection data are back-projected, and the generating of the first image may include generating the first image by correcting, based on the final weight map, N edge images respectively corresponding to the N pieces of projection data and representing edge information then back-projecting the corrected N edge images.

According to another embodiment of the present disclosure, an X-ray imaging apparatus includes: a memory storing N pieces of projection data (a projection data set) respectively corresponding to N views included in a first angular range; and a controller storing one or more instructions and including at least one processor configured to perform the stored one or more instructions. The processor may be configured to: generate a first image by back-projecting N edge images respectively representing edge information in the N pieces of projection data; generate a first corrected image by correcting a pixel value of a region corresponding to a material having a high X-ray attenuation rate compared to its surrounding region included in the first image; generate a frequency modulation-transformed first corrected image by performing frequency modulation transformation on the first corrected image; generate a filtered back-projection image by performing filtered back-projection on the N pieces of projection data; and generating a final tomography image by blending the frequency modulation-transformed first corrected image with the filtered back-projection image.

According to another embodiment of the present disclosure, a method of generating a tomography image includes: acquiring N pieces of projection data respectively corresponding to N views included in a first angular range by emitting X-rays toward an object while moving an X-ray source over the first angular range; generating M back-projection images respectively corresponding to M views among the N views, each of the M back-projection images representing a part of the object including a plurality of voxels, by back-projecting M pieces of projection data respectively corresponding to the M views; obtaining M first weight maps to be applied to the M back-projection images based on a mean value for voxels in the M back-projection images; generating M first corrected back-projection images respectively corresponding to the M views by applying the first weight maps respectively corresponding to the M back-projection images; obtaining N final weight maps applied when the N pieces of projection data are back-projected by using mean values of voxels in the M first corrected back-projection images; generating a first differentiated back-projection image by correcting N differentiated images respectively obtained via differentiation of the N pieces of projection data and then back-projecting the corrected N differentiated images; generating a first corrected differentiated back-projection image by correcting pixel values of a region corresponding to a material having a high X-ray attenuation rate compared to its surrounding region included in the first differentiated back-projection image; and generating a final tomography image by using the first differentiated back-projection image and the first corrected differentiated back-projection image.

MODE OF DISCLOSURE

The present specification describes principles of the disclosure and sets forth embodiments thereof to clarify the scope of claims of the disclosure and to allow those of ordinary skill in the art to implement the embodiments of the disclosure. The embodiments of the disclosure may be implemented in various forms.

Like reference numerals denote like elements throughout. The present specification does not describe all components in the embodiments, and common knowledge in the art or the same descriptions of the embodiments will be omitted below. Terms such as 'part' and 'portion' used herein denote those that may be embodied by software or hardware. According to embodiments, a plurality of 'parts' or 'portions' may be embodied by a single unit or element, or a single 'part' or 'portion' may include a plurality of units or elements. Hereinafter, the principles and embodiments of the present disclosure will be described in detail with reference to the accompanying drawings.

In the present specification, an image may include any medical image obtained by a medical imaging apparatus such as a magnetic resonance imaging (MRI) apparatus, a computed tomography (CT) apparatus, an ultrasound imaging apparatus, or an X-ray imaging apparatus.

In the specification, an 'object', which is a target to be imaged, may include a human, an animal, or a part thereof. For example, an object may include a body part (a vicarial organ or organ system) or a phantom.

FIG. 1 is an external view and block diagram of a configuration of an X-ray apparatus 100 according to an embodiment. In FIG. 1, it is assumed that the X-ray apparatus 100 is a fixed X-ray apparatus.

Referring to FIG. 1, the X-ray apparatus 100 includes an X-ray radiation device 110 for generating and emitting X-rays, an X-ray detector 200 for detecting X-rays that are emitted by the X-ray radiation device 110 and transmitted through an object P, and a workstation 180 for receiving a command from a user and providing information to the user. The X-ray apparatus 100 may further include a controller 120 for controlling the X-ray apparatus 100 according to the received command, and a communicator 140 for communicating with an external device.

All or some components of the controller 120 and the communicator 140 may be included in the workstation 180 or be separate from the workstation 180.

The X-ray radiation device 110 may include an X-ray source for generating X-rays and a collimator for adjusting a region irradiated with the X-rays generated by the X-ray source.

A guide rail 30 may be provided on a ceiling of an examination room in which the X-ray apparatus 100 is located, and the X-ray radiation device 110 may be coupled to a moving carriage 40 that is movable along the guide rail 30 such that the X-ray radiation device 110 may be moved to a position corresponding to the object P, and the moving carriage 40 and the X-ray radiation device 110 may be connected to each other via a foldable post frame 50 such that a height of the X-ray radiate on device 110 may be adjusted.

The workstation 180 may include an input device 181 for receiving a user command and a display 182 for displaying information.

The input device 181 may receive commands for controlling imaging protocols, imaging conditions, imaging timing, and locations of the X-ray radiation device 110. The input device 181 may include a keyboard, a mouse, a touch screen, a microphone, a voice recognizer, etc.

The display 182 may display a screen for guiding a user's input, an X-ray image, a screen for displaying a state of the X-ray apparatus 100, and the like.

The controller 120 may control imaging conditions and imaging timing of the X-ray radiation device 110 according to a command input by the user and may generate a medical image based on image data received from an X-ray detector 200. Furthermore, the controller 120 may control a position or orientation of the X-ray radiation device 110 or mounting units 14 and 24, each having the X-ray detector 200 mounted therein, according to imaging protocols and a position of the object P.

According to an embodiment of the disclosure, the controller 120 may control the X-ray radiation device 110 to emit X-rays while moving over a predetermined angular range. Accordingly, the X-ray radiation device 110 may emit X-rays toward the object from each of a plurality of views included in the predetermined angular range while moving over the predetermined angular range. Accordingly, the X-ray detector 200 may detect the X-rays passing through the object after being emitted by the X-ray radiation device 110. The controller 120 may acquire corresponding image data based on a result of the detection of the X-rays via the X-ray detector 200. An operation of emitting X-rays while moving over a predetermined angular range and acquiring data corresponding to the emitted X-rays will be described in detail below with reference to FIGS. 5 and 6.

The controller 120 may include a memory storing programs for performing the above-described operations and operations that will be described later and a processor configured to execute the stored programs. The controller 120 may include a single processor or a plurality of processors, and when the controller 120 includes the plurality of processors, the plurality of processors may be integrated onto a single chip or be physically separated from one another.

The X-ray apparatus 100 may be connected to external devices (such as an external server 191, a medical apparatus 192, and a portable terminal 193 (e.g., a smart phone, a tablet PC, a wearable device, etc.)) to transmit or receive data via the communicator 140.

The communicator 140 may include at least one component that enables communication with an external device and, for example, include at least one of a local area communication module, a wired communication module, or a wireless communication module.

Furthermore, the communicator 140 may receive a control signal from an external device and transmit the received control signal to the controller 120 so that the controller 120 may control the X-ray apparatus 100 according to the received control signal.

In addition, by transmitting a control signal to an external device via the communicator 140, the controller 120 may control the external device according to the control signal. For example, the external device may process data of the external device according to the control signal received from the controller 120 via the communicator 140.

The communicator 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 193, or a user of the portable terminal 193 may download the program from a server providing an application for installation. The server that provides applications may include a recording medium where the program is stored.

Furthermore, the X-ray detector 200 may be implemented as a fixed X-ray detector that is fixedly mounted to a stand 20 or a table 10 or as a portable X-ray detector that may be detachably mounted in the mounting unit 14 or 24 or may be used at arbitrary positions. The portable X-ray detector may be implemented as a wired or wireless detector according to a data transmission technique and a power supply method.

The X-ray detector 200 may or may not be included as a component of the X-ray apparatus 100. If the X-ray detector 200 is not included as a component of the X-ray apparatus 100, the X-ray detector 200 may be registered by a user with the X-ray apparatus 100. Furthermore, in both cases, the X-ray detector 200 may be connected to the controller 120 via the communicator 140 to receive a control signal from or transmit image data to the controller 120.

A sub-user interface 80 that provides information to a user and receives a command from the user may be provided on one side of the X-ray radiation device 110, and the sub-user interface 80 may also perform some or all of the functions performed by the input device 181 and the display 182 of the workstation 180.

When all or some components of the controller 120 and the communicator 140 are separate from the workstation 180, they may be included in the sub-user interface 80 provided on the X-ray radiation device 110.

Although FIG. 1 shows a fixed X-ray apparatus connected to the ceiling of the examination room, examples of the X-ray apparatus 100 may include a C-arm type X-ray apparatus, a mobile X-ray apparatus, and other X-ray apparatuses having various structures that will be apparent to those of ordinary skill in the art.

Figure 2:
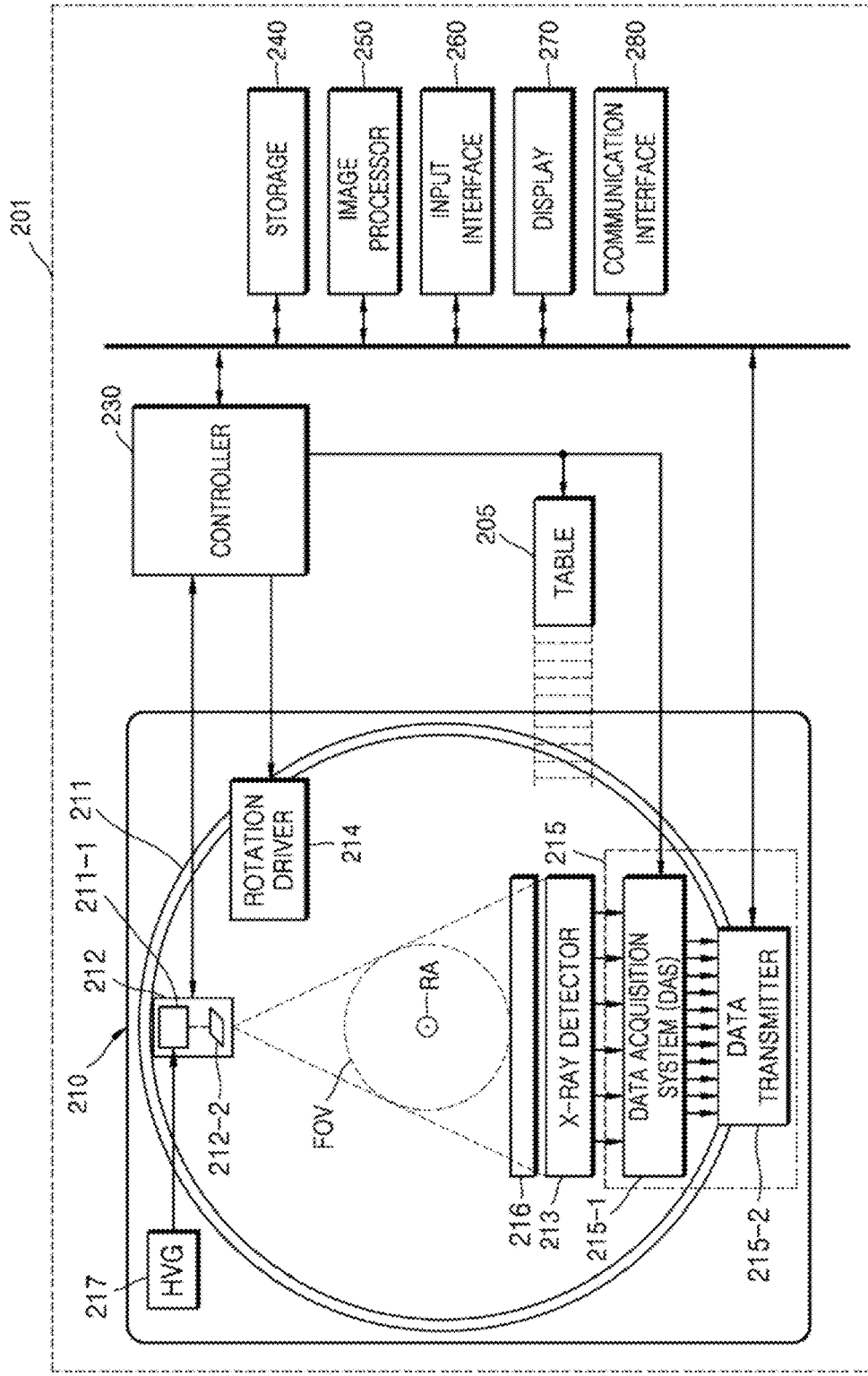
FIG. 2 illustrates a structure of a computed tomography (CT) system according to an embodiment.

FIG. 2 illustrates a structure of a CT system 201 according to an embodiment of the disclosure.

The CT system 201 may include a gantry 210, a table 205, a controller 230, a storage 240, an image processor 250, an input interface 260, a display 270, and a communication interface 280.

The gantry 210 may include a rotating frame 211, an X-ray generator 212, an X-ray detector 213, a rotation driver 214, and a readout device 215. The gantry 210 may further include a rotor rotating around an axis and a stator supporting the rotor.

The rotor may include the rotating frame 211, the X-ray generator 212, and the X-ray detector 213. The rotating frame 211 rotates around a predetermined rotation axis (RA) and may, for example, have a cylindrical or ring shape. According to control by the controller 230, the rotation driver 214 induces or creates a driving force for rotating the rotating frame 211 by using a motor and the like. As the rotating frame 211 rotates, the X-ray generator 212 and the X-ray detector 213 may rotate along a circumferential direction of the rotating frame 211. In addition, the rotor may include a slip ring that is in contact with the rotating frame 211 to transfer a signal or power and a bearing for minimizing a frictional force on the rotor.

The stator may support the rotor by using a housing, a fixing frame, or a RA bearing.

X-ray radiation that reaches the X-ray detector 213 includes attenuated primary radiation that forms an image and scattered radiation that deteriorates the quality of an image. An anti-scatter grid 216 may be positioned between an object and the X-ray detector 213 to transmit most of the primary radiation and attenuate the scattered radiation, thereby improving the quality of acquired medical image data.

The object may be positioned on the table 205 which may move, tilt, or rotate.

The X-ray generator 212 may receive a voltage and a current from a power distribution unit (PDU) via the slip ring and then a high voltage generator (HVG) 217 to generate and emit X-rays. For example, the X-rays emitted by the X-ray generator 212 may be shaped as a cone beam or a parallel beam.

The CT system 201 may be implemented as a single-source CT system including one X-ray generator 212 and one X-ray detector 213, or as a dual-source CT system including two X-ray generators and two X-ray detectors.

The X-ray detector 213 detects radiation that has passed through the object. For example, the X-ray detector 213 may detect radiation by using a scintillator, a photon counting detector, etc.

Methods of driving the X-ray generator 212 and the X-ray detector 213 may vary depending on scan modes used for scanning of the object. The scan modes are classified into an axial scan mode and a helical scan mode, according to a path along which the X-ray detector 213 moves. Furthermore, the scan modes are classified into a prospective mode and a retrospective mode, according to a time interval during which X-rays are emitted.

The controller 230 may control an operation of each of the components of the CT system 201. The controller 230 may include a memory storing a program or data for performing a function and a processor configured to process program codes or data. The controller 230 may be implemented in various combinations of at least one memory and at least one processor. The processor may generate or delete a program module according to an operation state of the CT system 201 and process operations of the program module.

According to an embodiment of the disclosure, the controller 230 may control the X-ray generator 212 to emit X-rays while moving over a predetermined angular range. Accordingly, the X-ray generator 212 may emit X-rays toward the object from each of a plurality of views included in the predetermined angular range while moving over the predetermined angular range. Accordingly, the X-ray detector 213 may detect the X-rays passing through the object after being emitted by the X-ray generator 212. The controller 230 may acquire corresponding image data based on a result of the detection of the X-rays via the X-ray detector 213. An operation of emitting X-rays while moving over a predetermined angular range and acquiring data corresponding to the emitted X-rays will be described in detail below with reference to FIGS. 5 and 6.

The readout device 215 receives a detection signal generated by the X-ray detector 213 and outputs the detection signal to the image processor 250. The readout device 215 may include a data acquisition system (DAS) 215-1 and a data transmitter 215-2. The DAS 215- amplifies a signal output from the X-ray detector 213 by using at least one amplifying circuit and outputs the amplified signal. The data transmitter 215-2 uses a circuit such as a multiplexer (MUX) to output the signal amplified in the DAS 215-1 to the image processor 250. According to a slice thickness or a number of slices, only some of a plurality of pieces of data collected by the X-ray detector 213 may be provided to the image processor 250.

The image processor 250 generates tomography data from a signal obtained by the readout device 215 (e.g., raw data before being processed). The image processor 250 may pre-process the obtained signal, convert the obtained signal into tomography data, and post-process the tomography data. The image processor 250 may perform some or all of the processes described herein, and the type or order of processes performed by the image processor 250 may vary according to an embodiment.

According to embodiments of the disclosure, the image processor 250 may perform some or all of the processes for reconstructing a tomography image to thereby generate the tomography data. According to an embodiment of the disclosure, the tomography data may be in the form of data that has undergone filtered back-projection, or in the form of a tomography image. According to embodiments of the disclosure, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 240 is a storage medium for storing control-related data, image data, etc., and may include a volatile or non-volatile storage medium.

The input interface 260 receives control signals, data, etc., from a user. For example, the control signals may include a control signal for controlling an imaging operation, a control signal for controlling display of a medical image, etc.

The display 270 may display information indicating an operation state of the CT system 201, medical information, medical image data, etc.

The CT system 201 includes the communication interface 280 and may be connected to external devices, such as a server, a medical apparatus, and a portable device (a smartphone, a tablet PC, a wearable device, etc.), via the communication interface 280.

The communication interface 280 may include at least one component that enables communication with an external device and, for example, include at least one of a local area communication module, a wired communication module, or a wireless communication module.

According to embodiments of the disclosure, the CT system 201 may or may not use contrast media during a CT scan, and may be implemented as a device connected to another equipment.

An X-ray imaging apparatus according to an embodiment of the present disclosure may be any imaging apparatus capable of generating or reconstructing a tomography image from data acquired by emitting X-rays towards an object. In this case, a tomography image may include any medical image obtained by three-dimensionally imaging an object via emission of X-rays. In detail, the tomography image may include a CT image, a tomosynthesis image, etc. In detail, an X-ray imaging apparatus according to an embodiment of the present disclosure may be the X-ray apparatus 100 illustrated in FIG. 1. Furthermore, an X-ray imaging apparatus according to an embodiment of the present disclosure may be the CT system 201 illustrated in FIG. 2. In addition, the X-ray apparatus 100 or the CT system 201 may correspond to a tomosynthesis system configured to acquire projection data while rotating over a predetermined angular range and generate a three-dimensional image (e.g., a tomosynthesis image) of the breast or the like.

In other words, an X-ray apparatus according to an embodiment of the present disclosure may be the X-ray apparatus 100, the CT system 201, or the tomosynthesis system.

Hereinafter, an example in which a tomography image reconstructed according to an embodiment of the present disclosure is a tomosynthesis image will be described.

An X-ray imaging apparatus according to an embodiment of the present disclosure (e.g., 300 of FIG. 3 or 400 of FIG. 4) may exist in various forms. For example, an X-ray imaging apparatus according to an embodiment of the present disclosure may be included in the workstation 180 of the X-ray apparatus 100 of FIG. 1 or the controller 210 or image processor 250 of the CT system 201 of FIG. 2.

As another example, an X-ray imaging apparatus according to an embodiment of the present disclosure may be provided on a separate device or server that is independent from a medical imaging apparatus such as the X-ray apparatus 100 of FIG. 1 and the CT system 201 of FIG. 2. In this case, the separate device or server that is independent from the medical imaging apparatus may be referred to as an 'external device'. For example, the external device may be the server 191, the medical apparatus 192, and the portable terminal 193 illustrated in FIG. 1.

In addition, the external device may be any other electronic device capable of receiving data acquired by emitting X-rays toward an object (specifically, a plurality of pieces of projection data respectively corresponding to a plurality of views) and generating or reconstructing a tomography image from the received data. For example, an X-ray imaging apparatus according to an embodiment of the present disclosure may be provided on an analysis workstation, an external medical apparatus, a picture archiving communications system (PACS) server, a PACS viewer, an external medical server, or a hospital server.

An X-ray imaging apparatus according to an embodiment of the present disclosure will be described in detail with reference to FIGS. 3 and 4. Furthermore, detailed operations of the X-ray imaging apparatus and a tomography image generation method according to embodiments of the present disclosure will be described in detail with reference to FIGS. 3 through 12.

Figure 3:
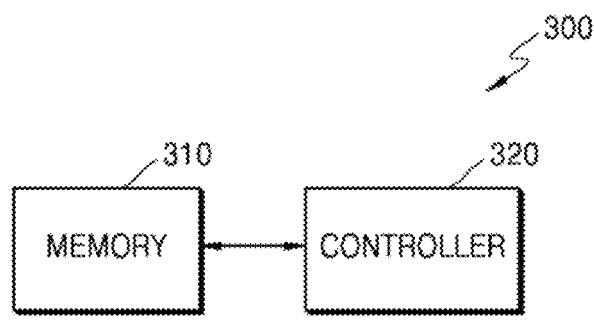
FIG. 3 illustrates an X-ray imaging apparatus according to an embodiment of the present disclosure.

FIG. 3 illustrates an X-ray imaging apparatus according to an embodiment of the present disclosure.

Referring to FIG. 3, an X-ray imaging apparatus 300 according to an embodiment of the present disclosure includes a memory 310 and a controller 320.

The X-ray imaging apparatus 300 according to the embodiment of the present disclosure acquires N pieces of projection data respectively corresponding to N views included in the first angular range and generates a tomography image with reduced ripple artifacts or undershooting artifacts by using the acquired N pieces of projection data.

The memory 310 stores N pieces of projection data respectively corresponding to the N views included in the first angular range. In this case, the memory 310 may be any storage medium for storing the N pieces of projection data (for example, a projection data set) acquired by emitting X-rays toward the object.

Here, the object may be a part of a patient's body being examined, for which a medical image is to be acquired, and may be a body part corresponding to the breast, chest, joint, or the like.

When the X-ray imaging apparatus 300 is provided on the workstation 180 of the X-ray apparatus 100 of FIG. 1, the controller 320 may control the N pieces of projection data, which is data acquired by performing X-ray imaging, to be stored in the memory 310. Furthermore, when the X-ray imaging apparatus 300 is provided as a separate device from the X-ray apparatus 100, the X-ray imaging apparatus 300 may receive N pieces of projection data (a projection data set) that are data acquired when the X-ray apparatus 100 performs X-ray imaging and store the received N pieces of projection data in the memory 310.

Furthermore, when the X-ray imaging apparatus 300 is provided in the CT system 201 of FIG. 2, the controller 320 may control N pieces of projection data that are data acquired by performing a CT scan to be stored in the memory 310. Furthermore, when the X-ray imaging apparatus 300 is provided as a separate device from the X-ray apparatus 100, the X-ray imaging apparatus 300 may receive N pieces of projection data, which are data acquired when the X-ray apparatus 100 performs X-ray imaging, and store the received N pieces of projection data in the memory 310.

In addition, the memory 310 may include at least one type of storage medium from among a flash memory-type memory, a hard disk-type memory, a multimedia card micro-type memory, a card-type memory (e.g., an SD or XD memory), random access memory (RAM), static RAM (SRAM), read-only memory (ROM), electrically erasable programmable ROM (EEPROM), PROM, a magnetic memory, a magnetic disc, and an optical disc.

The controller 320 stores one or more instructions and includes at least one processor (not shown) for executing the stored one or more instructions.

Operations performed in an embodiment of the present disclosure may be performed according to control by the controller 320. In detail, at least one processor (not shown) in the controller 320 may operate to perform a predetermined operation by executing at least one instruction stored in the controller 320 or the memory 310.

Furthermore, the controller 320, and in particular, a processor (not shown) included in the controller 320, obtains a weight map applied to N pieces of projection data based on M pieces of projection data respectively corresponding to M views that are some of N views.

In detail, the controller 320 obtains a final weight map applied when the N pieces of projection data are back-projected based on the M pieces of projection data respectively corresponding to the M views that are some of the N views.

Then, the controller 320 generates a final tomography image showing the object by using the final weight map and the N pieces of projection data.

In detail, the controller 320 may generate a final tomography image by applying a final weight map when the N pieces of projection data are back-projected such that the above-described metal artifacts are reduced.

An element having a large attenuation coefficient of X-rays may exist in the object. For example, metal pins may be inserted into a patient's leg bone in a surgery to fix the leg bone using the metal pins, etc., or a stent made of a metallic material may be placed in a patient who has undergone a stent procedure in order to widen the blood vessels.

Metallic materials such as metal pins have a very large attenuation coefficient of X-rays. Thus, when the object is a body part of a patient into which a metallic material is inserted, the metallic material inserted into the object almost absorbs the emitted X-rays during X-ray imaging. In this case, because a portion where the metallic material is located and even a surrounding region adjacent thereto exhibit very high signal intensity values in an X-ray image, an original shape of the object may appear distorted in the X-ray image. In this way, image distortion caused by a metallic material in an X-ray image may be referred to as 'out-of-plane artifacts' or 'metal artifacts', such as 'ripple artifacts' or 'undershoot artifacts'. All artifacts appearing in an X-ray image due to such metallic materials will be hereinafter referred to as metal artifacts.

Figure 15A:
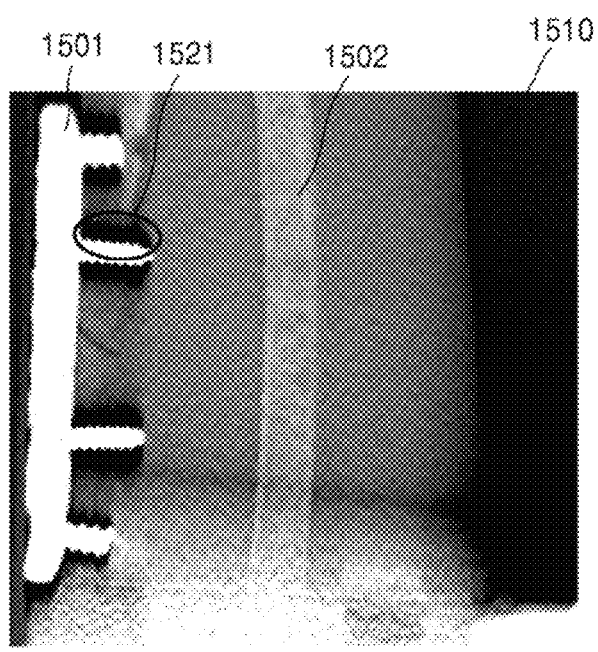
FIG. 15A illustrates a tomography image obtained according to a conventional tomography image generation method.

In detail, FIG. 15A illustrates an X-ray image 1510 captured when a metal pin 1501 is embedded in a bone 1502 in a patient's arm.

In the X-ray image 1510, the metal pin 1501 is shown as abnormally bright, and a region surrounding the metal pin 1501 appears distorted when imaged. In this case, a region shown as abnormally bright, such as a region in which the metal pin 1501 is imaged, may be referred to as an outlier region. In detail, an afterimage such as a dark region 1521 appears around the metal pin 1501. In this case, an artifact that appears as an afterimage in the X-ray image 1510 is referred to as an undershoot artifact. In addition, an artifact in which a material included in the object, such as the metal pin 1501, appears to be repeatedly imaged is referred to as a ripple artifact. Thus, a correction value applied to prevent an image from being distorted by removing or reducing such ripple artifacts and/or undershoot artifacts may be a final weight map.

The controller 320 may also reconstruct a final tomography image by using the final weight map and N pieces of projection data.

Two reconstruction methods may be mainly used to reconstruct a tomography image by using N pieces of projection data which are raw data acquired via X-ray imaging. A first reconstruction method involves performing edge enhancement and then back-projection on N pieces of projection data (e.g., performing differentiated back-projection on the N pieces of projection data) and generating a tomography image by continuously performing frequency modulation transformation such as Hilbert transform. A second reconstruction method is a method of generating a tomography image by performing filtered back-projection (FBP) on N pieces of projection data, i.e., by filtering the N pieces of projection data before back-projection.

Accordingly, the controller 320 may control a tomography image to be reconstructed by applying a final weight map when the N pieces of projection data are back-projected.

For example, when a final tomography image is generated according to the above-described first reconstruction method, the controller 320 may generate a first differentiated back-projection image by correcting N differentiated images respectively obtained via differentiation of N pieces of projection data and then back-projecting the corrected N differentiated images. Then, the controller 320 may operate to generate a final tomography image showing the object by using the first differentiated back-projection image.

Operations of generating a final tomography image according to the above-described first reconstruction method will be described in detail below with reference to FIGS. 9B through 12B. Furthermore, operations of generating a final tomography image according to the second reconstruction method will be described in detail below with reference to FIGS. 13 and 14.

In detail, the controller 320 may internally include a memory such as ROM, RAM, etc., and at least one processor that performs instructions for performing the above-described operations. In addition, the at least one processor included in the controller 320 may operate to execute instructions for performing the above-described operations.

Figure 4:
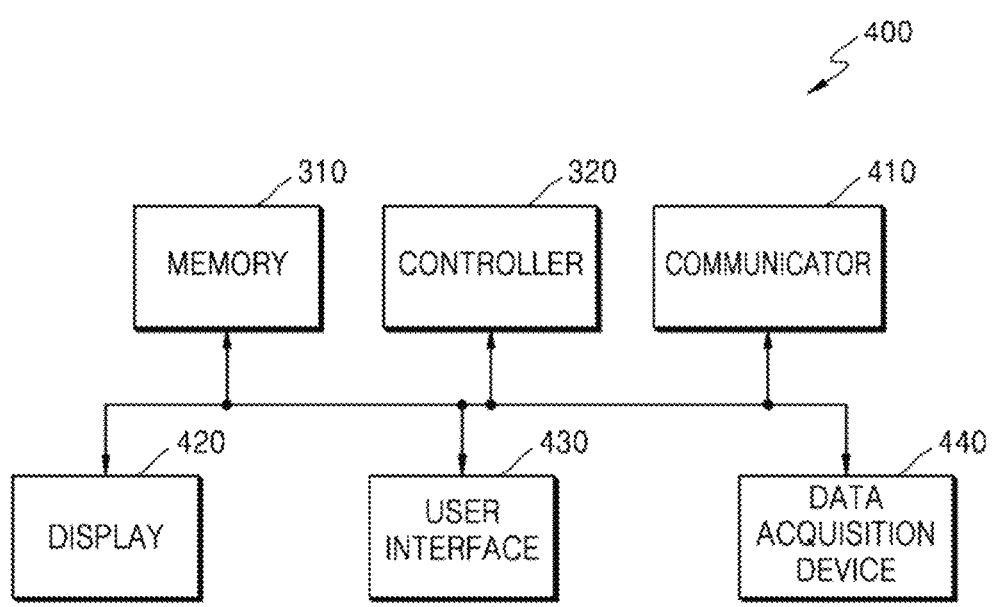
FIG. 4 illustrates an X-ray imaging apparatus according to another embodiment of the present disclosure.

FIG. 4 illustrates an X-ray imaging apparatus 400 according to another embodiment of the present disclosure. The same components of the X-ray imaging apparatus 400 illustrated in FIG. 4 as those of the X-ray imaging apparatus 300 of FIG. 3 are represented by the same reference numbers. Thus, descriptions that are already provided above with respect to FIG. 3 will be omitted herein.

Referring to FIG. 4, the X-ray imaging apparatus 400 may further include at least one of a communicator 410, a display 420, a user interface 430, or a data acquisition device 440 compared to the X-ray imaging apparatus 300.

The communicator 410 may transmit or receive data to or from an external electronic device (not shown) through a wired or wireless communication network. In detail, the communicator 410 may transmit/receive data according to control by the controller 320. In this case, the communicator 410 may correspond to the communicator 140 shown in FIG. 1 or the communication interface 280 shown in FIG. 2.

Furthermore, an external electronic device (not shown) connected to the communicator 410 via a wired or wireless communication network may be the server 191, the medical apparatus 192, or the portable terminal 193 shown in FIG. 1. Furthermore, the external electronic device may be any medical imaging apparatus that is provided independently of the X-ray imaging apparatus 400.

In an embodiment of the present disclosure, the communicator 410 may receive data acquired via X-ray imaging from the external electronic device. In detail, the communicator 410 may receive N pieces of projection data respectively corresponding to N views included in a first angular range from the external electronic device.

Alternatively, the communicator 410 may receive data for generating the N pieces of projection data respectively corresponding to the N views included in the first angular range. In this case, the received data may be converted into the N pieces of projection data according to control by the controller 320. Alternatively, according to control by the controller 320, the N pieces of projection data may be generated based on the received data.

The display 420 displays image data that is visually recognizable by the user.

In detail, the display 420 may display a medical image, a user interface screen, user information, and image processing information. In an embodiment of the present disclosure, the display 420 may display a final tomography image generated according to control by the controller 320. In addition, according to control by the controller 320, the display 420 may display, on a single screen, a final tomography image where metal artifacts are reduced or removed by using a final weight map according to an embodiment of the disclosure and a tomography image reconstructed using a conventional method without applying the final weight map by including them in the single screen.

The user interface 430 may receive predetermined data or a predetermined command from the user. The user interface 430 may correspond to at least one of the sub-user interface 80 or the input device 181 of FIG. 1. Furthermore, the user interface 430 may be formed as a touch screen integrated with the display 420. As another example, the user interface 430 may include a user input device such as a pointer, a mouse, a keyboard, etc.

In an embodiment of the present disclosure, the user interface 430 may receive information for setting M views among the N views. In detail, the user interface 430 may receive criteria for selecting M views among the N views included in the first angular range, such as an angular interval, the number of M, etc.

The data acquisition device 440 may be a medical imaging apparatus for acquiring N pieces of projection data respectively corresponding to the N views included in the first angular range For example, the data acquisition device 440 may include the X-ray radiation device 110 and the X-ray detector 200 described with reference to FIG. 1 and perform an operation for acquiring N pieces of projection data as described with reference to FIG. 5. When the X-ray imaging apparatus 400 includes the data acquisition device 440, the X-ray imaging apparatus 400 may correspond to the X-ray apparatus 100 described with reference to FIG. 1.

As another example, the data acquisition device 440 may include the X-ray generator 212 and the X-ray detector 213 described with reference to FIG. 2 to perform an operation for acquiring N pieces of projection data described with reference to FIG. 5. When the X-ray imaging apparatus 400 includes the data acquisition device 440, the X-ray imaging apparatus 400 may correspond to the CT system 201 described with reference to FIG. 2.

The N pieces of projection data (a projection data set) and M pieces of projection data used in an embodiment of the present disclosure will be described in detail below with reference to FIGS. 5 and 6.

The N pieces of projection data used in an embodiment of the present disclosure may be acquired by a medical imaging apparatus (not shown). The medical imaging apparatus refers to any medical imaging apparatus capable of moving over a predetermined angular range, irradiating an object with X-rays from each of a plurality of views included in a predetermined angular range, and acquiring projection data by detecting the X-rays passing through the object. The medical imaging apparatus may be the X-ray imaging apparatus 300 of FIG. 1 or the CT system 201 of FIG. 2.

X-rays are electromagnetic waves with a short wavelength generated when an electron ray emerging from a cathode at high speed in vacuum discharges collides with a heavy metal, and have a very high transmittance through an object and produce fluorescence. Thus, when X-rays are emitted toward an object, some of the X-rays are absorbed and attenuated by the object to thereby detect a change in density or thickness inside the object. The medical imaging apparatus acquires projection data which is data representing a shape and a structure of the inside of the object, by using such characteristics of X-rays.

Figure 5:
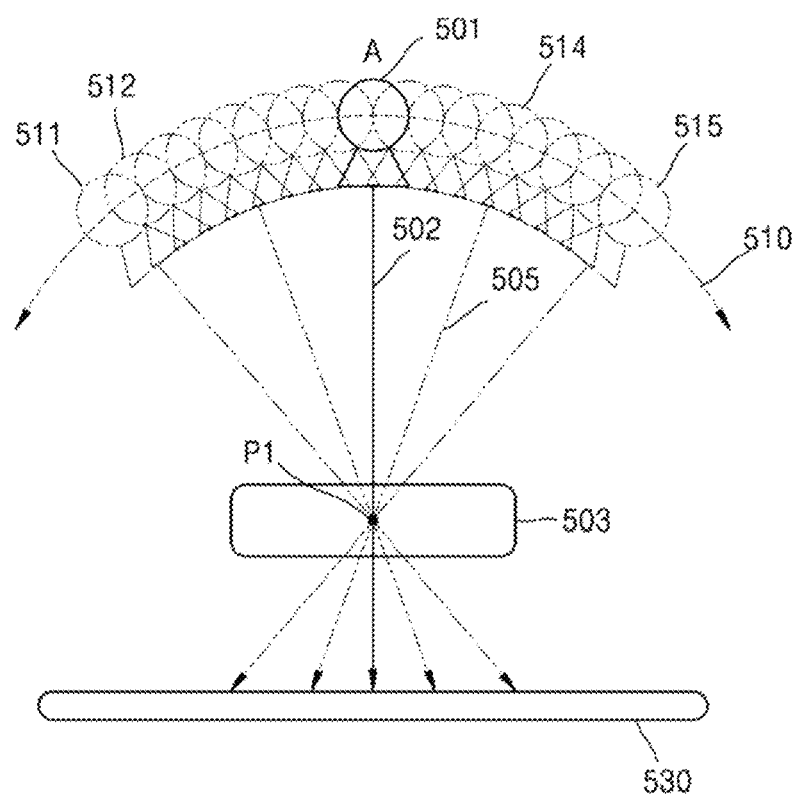
FIG. 5 is a diagram for explaining an operation of acquiring N pieces of projection data used in an embodiment of the present disclosure.

FIG. 5 is a diagram for describing an operation of acquiring N pieces of projection data used in an embodiment of the present disclosure Referring to FIG. 5, the medical imaging apparatus includes an X-ray radiation device 501 and an X-ray detector 530. Here, the X-ray radiation device 501 generates X-rays and emits the X-rays toward a predetermined region of an object 503, for example, a body part to be examined. The X-ray radiation device 501 may generate and emit X-rays while moving in a predetermined angular range. In detail, the X-ray radiation device 501 may move through a curved path that is a path 510 shown in FIG. 5.

Because the X-ray radiation device 501 corresponds to each of the X-ray radiation device 110 of FIG. 1 and the X-ray generator 212 of FIG. 2, a detailed description thereof will be omitted here. Furthermore, because the X-ray detector 530 corresponds to each of the X-ray detector 200 of FIG. 1 and the X-ray detector 213 of FIG. 2, a detailed description thereof will be omitted here.

According to an embodiment of the present disclosure, the medical imaging apparatus emits X-rays respectively from N views included in a first angular range and acquires N pieces of projection data corresponding to the N views.

Referring to FIG. 5, the first angular range may be an angular range from a position 511 to a position 515, over which the X-ray radiation device 501 moves about a reference point P1. Furthermore, the N views are included in the first angular range. In addition, while moving the X-ray radiation device 501 within the first angular range, the medical imaging apparatus may emit X-rays toward the object in each of the N views, which are a plurality of views, via the X-ray radiation device 501.

In detail, as the X-ray radiation device 501 of the medical imaging apparatus rotates around the object 503 of a patient, the medical imaging apparatus acquires projection data that is raw data acquired at each rotation angle with respect to the object 503. The medical imaging apparatus may include at least one X-ray radiation device 501 to acquire projection data.

In detail, the X-ray radiation device 501 emits X-rays toward the object 503 from a predetermined view corresponding to each rotation angle while rotating around a center of the object 503 (e.g., position P1) as an axis. For example, the X-ray radiation device 501 stops at a position 511 corresponding to one rotation angle to emit X-rays and then moves to a position 512 corresponding to another rotation angle and stops to emit X-rays. Such a rotation angle may be arbitrarily set and changed by the user according to a usage environment.

Furthermore, the X-ray detector 530 detects each of the X-rays emitted and transmitted through the object 503 as described above, and acquires X-ray data (in particular, projection data or an X-ray image corresponding to the projection data) based on the detected X-rays. In this case, the X-ray detector 530 may map and store information about a rotation angle at which the X-ray data is acquired.

Here, X-ray images respectively captured at rotation angles may be obtained under the same X-ray dose condition. In general, the degree to which X-rays may penetrate the object 503 varies depending on an X-ray dose indicating an intensity of the X-rays. Thus, the user of the medical imaging apparatus may set a condition of X-ray dose for imaging before the imaging starts. Furthermore, the condition of the X-ray dose may be changed by a user's input before the imaging starts.

In an embodiment of the present disclosure, the first angular range may be set to a total angular range of 60 degrees between 30 degrees to the left and 30 degrees to the right relative to position A. Alternatively, the first angular range may be set to a total angular range of 40 degrees between 20 degrees to the left and right relative to a central position. Furthermore, the first angular range may be an angular range having a value between 40 and 60 degrees as an angular range having a shape symmetric about a reference point.

In addition, the number of a plurality of views included in the first angular range may be 50. For example, when the first angular range is 50 degrees, the 50 degrees may be divided into 50 to set views at 1-degree intervals, and the X-ray radiation device 501 may emit 50 X-rays from each of the 50 views while moving by a 1 degree. Accordingly, the X-ray detector 530 may detect X-rays corresponding to the 50 views based on the X-rays respectively emitted from the 50 views. In this case, the medical imaging apparatus may acquire 50 pieces of X-ray data (e.g., projection data). In this way, a plurality of pieces of projection data respectively acquired from the plurality of views in the first angular range may be referred to as a 'projection data set corresponding to the first angular range'. In addition, initially acquired projection data may be referred to as raw data.

Figure 6:
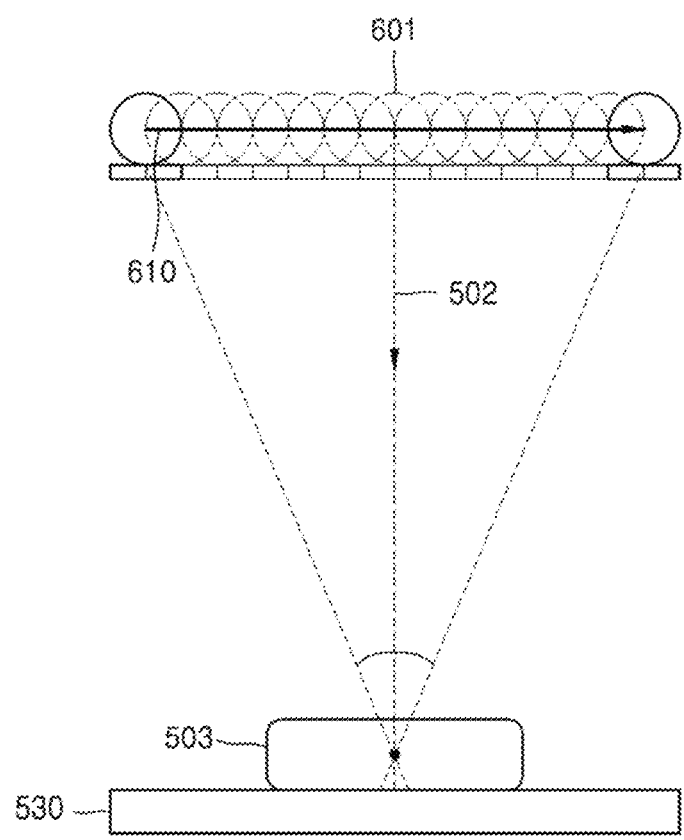
FIG. 6 is another diagram for explaining an operation of acquiring N pieces of projection data used in an embodiment of the present disclosure.

FIG. 6 is another diagram for explaining an operation of acquiring N pieces of projection data used in an embodiment of the present disclosure. The X-ray radiation device 601 shown in FIG. 6 corresponds to the X-ray radiation device 501 shown in FIG. 5. However, the X-ray radiation device 601 shown in FIG. 6 moves along a straight-line path 610 other than a rotation path like the path 510.

In other words, the embodiment shown in FIG. 6 is different from the embodiment shown in FIG. 5 only in a path along which the X-ray radiation device 601 moves over a first angular range. Since the other components are all the same as those in the embodiment shown in FIG. 5 and are represented by the same reference numerals, detailed descriptions thereof will be omitted here.

In an embodiment of the present disclosure, the controller 320, and in particular, a processor (not shown) included in the controller 320, obtains a final weight map applied to the N pieces of projection data based on M pieces of projection data respectively corresponding to M views which are some of the N views.

In this case, the M pieces of projection data respectively corresponding to the M views will be described in detail below with reference to FIG. 7.

Figure 7:
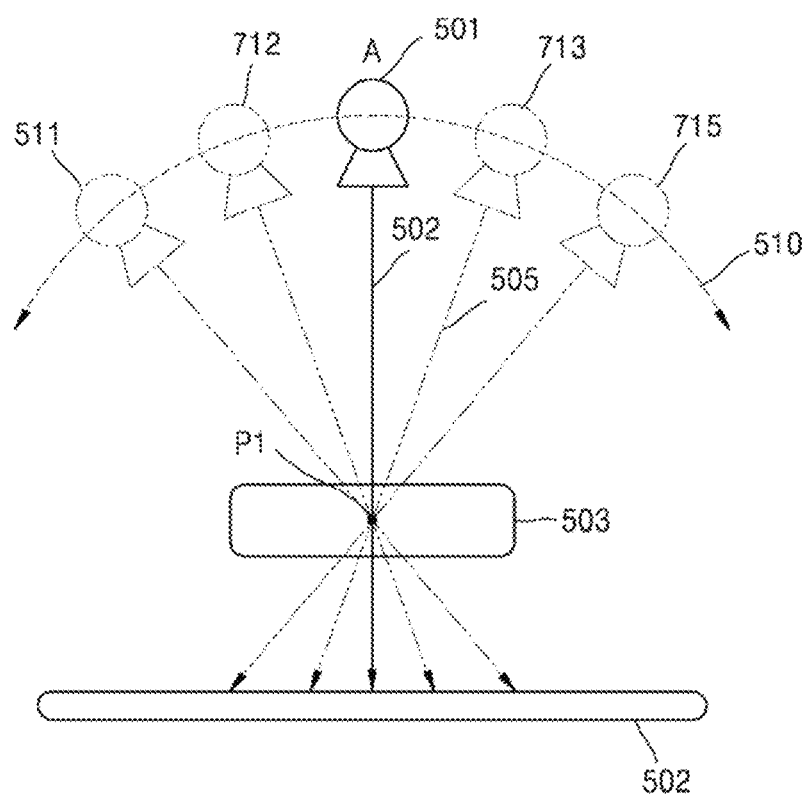
FIG. 7 is a diagram for explaining M pieces of projection data used in an embodiment of the present disclosure.

FIG. 7 is a diagram for explaining M pieces of projection data used in an embodiment of the present disclosure. In FIG. 7, the same components as those in the embodiment shown in FIG. 5 are represented by the same reference numerals.

Referring to FIG. 5, a first angular range may be an angular range from a position 511 to a position 715, over which the X-ray radiation device 501 moves about a reference point P1, and the M v In an embodiment of the present disclosure, the M pieces of projection data respectively corresponding to the M views, which are some of the N views, are used in order to obtain a final weight map applied to the N pieces of projection data.

In detail, the M views may be views extracted at predetermined intervals from among the N views included in the first angular range. Here, M is an integer value less than or equal to N.

Referring to FIG. 7, the M views may be extracted at equal angular intervals from among N views that are a plurality of views included in the first angular range. For example, the first angular range may have a value of 50 degrees. Furthermore, according to the embodiment, FIG. 7 shows an example in which N=50 and M=5.

In addition, an example in which the first angular range includes first through fiftieth views at 1-degree intervals is shown. Here, N may be 50. In this case, position 511 may correspond to a first view, position 712 with an interval of 10 degrees away from the position 511 may correspond to an eleventh view, position A with an interval of 10 degrees away from the position 712 may correspond to a twenty-first view, position 713 with an interval of 10 degrees away from position A may correspond to a thirty-first view, and position 715 with an interval of 10 degrees away from the position 713 may correspond to a forty-first view. In other words, views arranged at 1-degree intervals in the first angular range may be referred to as first through fiftieth views.

Furthermore, the M views may be views extracted at unequal, random intervals among the N views.

In addition, the M pieces of projection data may be selected among the N pieces of projection data in an experimentally optimized manner. In detail, the M pieces of projection data may be experimentally selected among the N pieces of projection data at equal angular intervals or random angular intervals in a direction in which the quality of an obtained final tomography image is improved.

Figure 8:
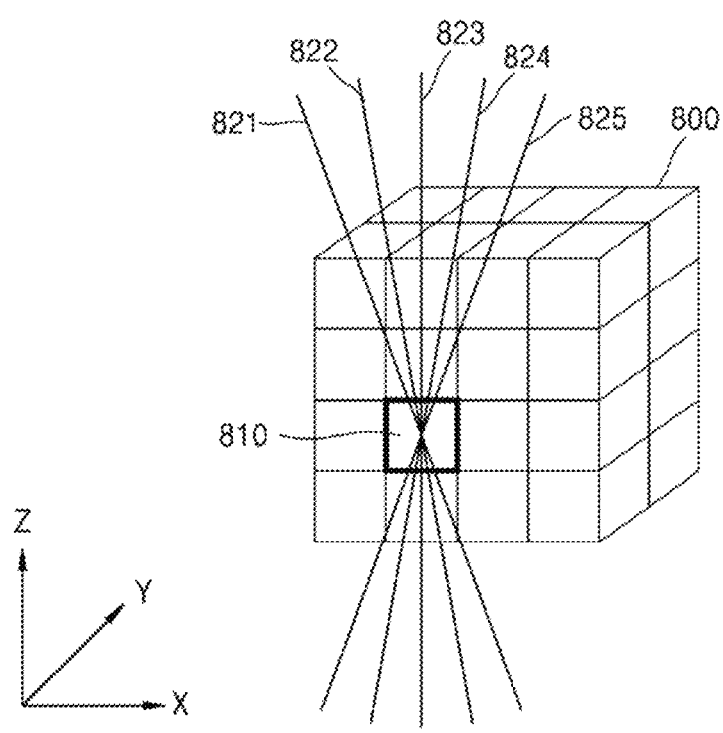
FIG. 8 is a diagram for representing a portion of an object to be imaged as a plurality of voxels, according to an embodiment of the present disclosure.

FIG. 8 is a diagram for representing a portion of an object to be imaged as a plurality of voxels according to an embodiment of the present disclosure.

In an embodiment of the present disclosure, an object irradiated with X-rays may be represented as a voxel region 800 composed of voxels. The voxel region 800 is a conceptual three-dimensional space and may include a plurality of voxels in the X-, Y-, and Z-axis directions.

Referring to FIGS. 5, 7 and 8, view 821 is a view in which the X-ray radiation device 501 emits an X-ray toward the voxel region 800 of the object at the position 511. Furthermore, view 822 is a view in which the X-ray radiation device 501 emits an X-ray toward the voxel region 800 of the object at the position 712. View 823 is a view in which the X-ray radiation device 501 emits an X-ray toward the voxel region 800 of the object at the position A. In addition, view 824 is a view in which the X-ray radiation device 501 emits an X-ray toward the voxel region 800 of the object at the position 713, and view 825 is a view in which the X-ray radiation device 501 emits an X-ray toward the voxel region 800 of the object at the position 515. In other words, the first view, the eleventh view, the twenty-first view, the thirty-first view, and the forty-first view described with reference to FIG. 7 may be views 821 through 825, respectively.

Furthermore, pieces of projection data acquired by emitting X-rays from the first view (821), the eleventh view (822), the twenty-first view (823), the thirty-first view (824), and the forty-first view (825) may be respectively referred to as first projection data, eleventh projection data, twenty-first projection data, thirty-first projection data, and forty-first projection data.

Referring to FIG. 8, a process of emitting an X-ray toward an object from a predetermined view may be referred to as a "projection process". Furthermore, a process of obtaining, as a data value, an X-ray detected by emitting an X-ray toward an object from a predetermined view may also be referred to as a 'projection process'.

In detail, the projection process may be defined as a process of obtaining raw data that is a value corresponding to an attenuation coefficient of an X-ray that passes through a portion of the object corresponding to a voxel 810 to be imaged along a radiated path of an X-ray (e.g., an X-ray emitted from the view 821). That is, the raw data may be projection data.

In addition, a process of reconstructing an image showing an object by accumulating, for each view, raw data which are values corresponding to X-ray attenuation coefficients obtained during a projection process may be referred to as a 'back-projection process'.

Figure 9A:
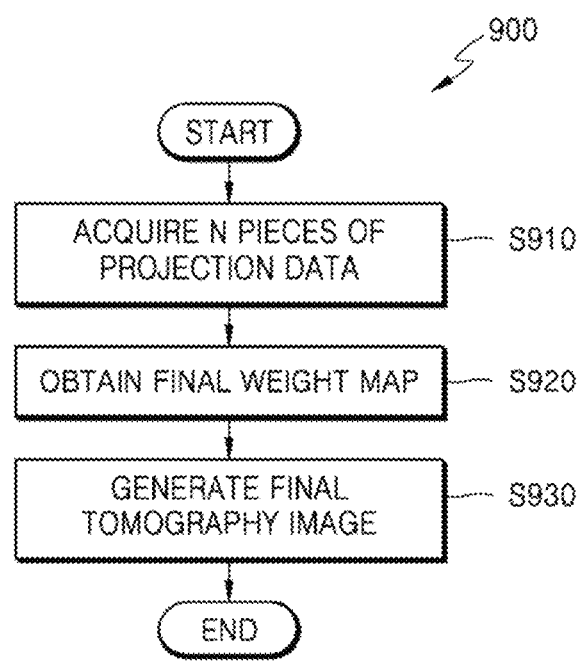
FIG. 9A is a flowchart of a tomography image generation method according to an embodiment of the present disclosure.

FIG. 9A is a flowchart of a tomography image generation method according to an embodiment of the present disclosure.

Figure 9B:
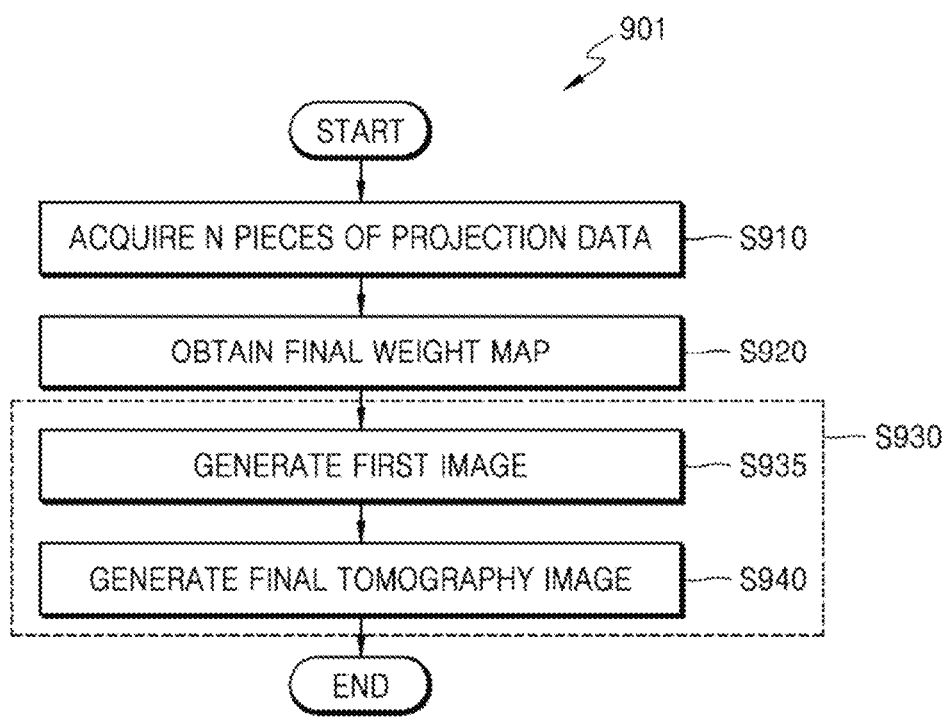
FIG. 9B is another flowchart of a tomography image generation method according to an embodiment of the present disclosure.

FIG. 9B is another flowchart of a tomography image generation method according to an embodiment of the present disclosure.

Figure 9C:
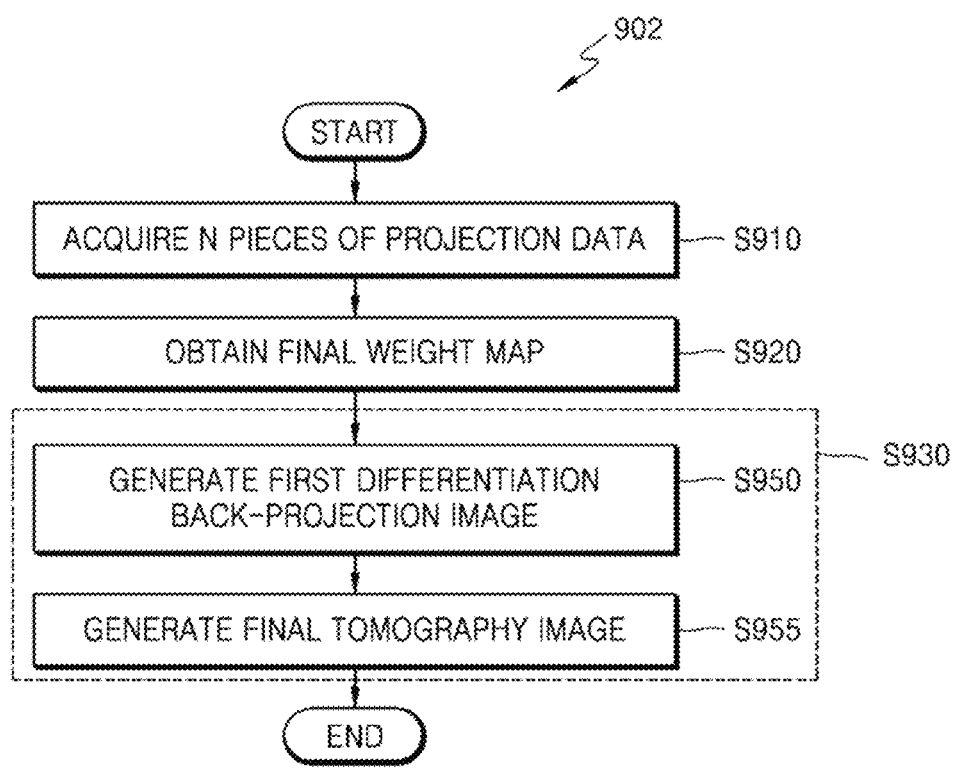
FIG. 9C is another flowchart illustrating a tomography image generation method according to an embodiment of the present disclosure.

FIG. 9C is another flowchart illustrating a tomography image generation method according to an embodiment of the present disclosure.

Furthermore, the X-ray imaging apparatus 300 according to the embodiment of the present disclosure may perform operations according to each of the flowcharts illustrated in FIGS. 9A through 9C.

Thus, hereinafter, a tomography image generation method according to one or another embodiment of the present disclosure and detailed operations of the X-ray imaging apparatus 300 according to the tomography image generation method will be described with reference to FIGS. 9A and 14.

Referring to FIG. 9A, in a tomography image generation method 900, N pieces of projection data (a projection data set) respectively corresponding to N views included in a first angular range are acquired (S910). The X-ray imaging apparatus 300 may acquire the N pieces of projection data respectively corresponding to the N views included in the first angular range and store the N pieces of projection data in the memory 310. In detail, the N pieces of projection data may be stored in the memory 310 according to control by the controller 320.

Then, final weight maps applied to the N pieces of projection data are obtained based on M pieces of projection data respectively corresponding to M views that are some of the N views (S920). In detail, final weight maps applied when the N pieces of projection data are back-projected may be obtained based on the M pieces of projection data respectively corresponding to the M views among the N views. Operation S920 may be performed by the controller 320. An operation of obtaining a final weight map applied to the N pieces of projection data will be described in detail with reference to FIG. 10.

A final tomography image showing an object is generated by using the final weight map obtained in operation S920 and the N pieces of projection data obtained in operation S910 (S930). Here, the final tomography image may include a tomosynthesis image. Furthermore, the object may be at least a patient's body part such as legs, chest, and arms. Operation S920 may be performed by the controller 320. Hereinafter, operation S930 will be described in detail with reference to FIGS. 9B and 9C.

FIG. 9B is another flowchart of a tomography image generation method according to an embodiment of the present disclosure. Because the same components in FIG. 9B as those in FIG. 9A are represented by the same reference numerals, descriptions that are already provided above with respect to FIG. 9A will be omitted when describing a tomography image generation method 901 illustrated in FIG. 9B.

Referring to FIG. 9B, an operation S930 of generating a final tomography image may include generating a first image (S935) and generating the final tomography image by using the first image and the final weight map (S940).

In detail, in the tomography image generation method 901, the first image may be generated by correcting N edge images using the final weight map obtained in operation S920 and then back-projecting the corrected N edge images, the N edge images respectively representing edge information in the N pieces of projection data acquired in operation S910 (S935). Operation S935 may be performed by the controller 320.

In this case, edge information refers to information about a surface and/or an edge representing components forming or included in an object when all components (e.g., bones, organs, tissues, or implants) forming or included in the object are captured in a tomography image of the object. In detail, when each of the N pieces of projection data is differentiated, a surface and/or an edge in each of the N pieces of projection data appears sharper. In this case, N differentiated images obtained by respectively differentiating the N pieces of projection data may be edge images respectively corresponding to the N pieces of projection data. In addition, although a differentiated image has been described as an example of an edge image representing edge information, the edge image may include all other images obtained by performing processing for enhancing an edge or surface being imaged in the object.

Then, the final tomography image may be generated using the first image (S940). Operation S940 may be performed by the controller 320. Operation S940 will be described in more detail with reference to FIG. 11.

FIG. 9C is another flowchart illustrating a tomography image generation method according to an embodiment of the present disclosure. Because the same components in FIG. 9C as those in FIG. 9A are represented by the same reference numerals, descriptions that are already provided above with respect to FIG. 9A will be omitted when describing a tomography image generation method 902 illustrated in FIG. 9C.

Referring to FIG. 9C, an operation S930 of generating a final tomography image may include generating a first differentiated back-projection image (S950) and generating the final tomography image by using the first differentiated back-projection image (S955). Furthermore, operations S950 and S955 of FIG. 9C may respectively correspond to operations S935 and S940 of FIG. 9B.

In detail, in the tomography image generation method 902, N differentiated images obtained by respectively differentiating the N pieces of projection data are corrected using the final weight map obtained in operation S920. Then, a first differentiated back-projection image is generated by back-projecting the corrected N differentiated images (S950). Operation S950 may be performed by the controller 320.

The final tomography image showing the object is generated by using the first differentiated back-projection image obtained in operation S950 (S955). Operation S955 may be performed by the controller 320. The operation of generating the final tomography image will be described in more detail below with reference to FIGS. 11 through 12B.

Figure 10:
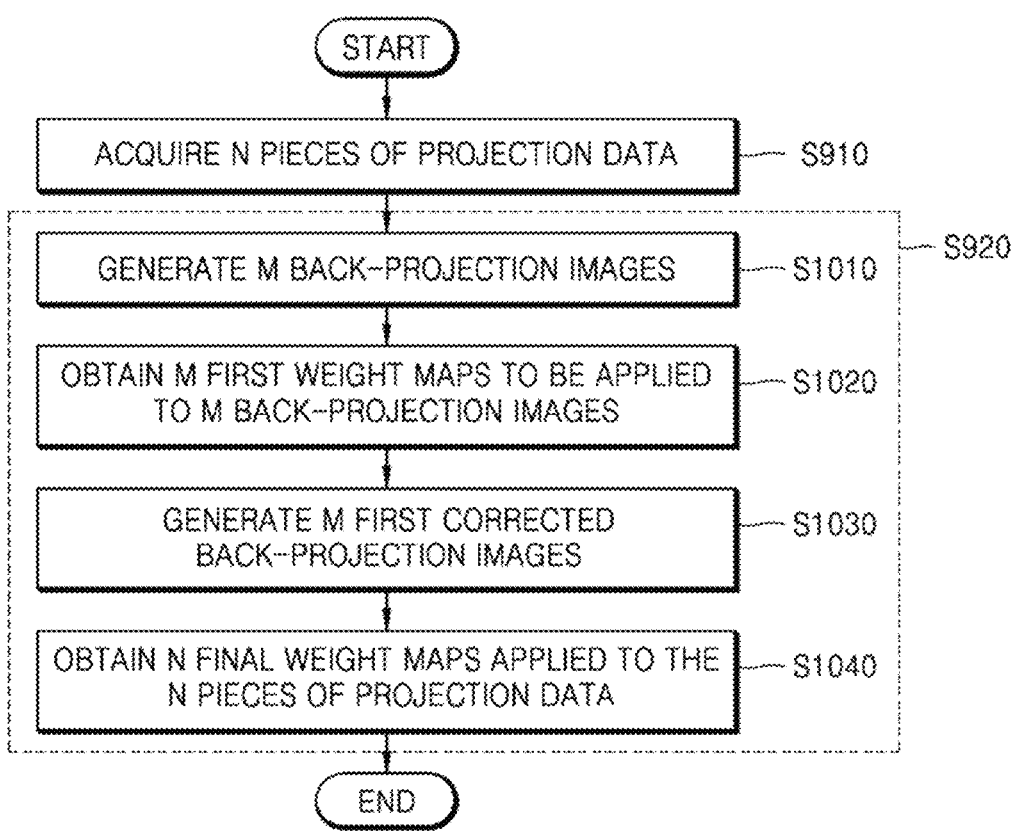
FIG. 10 illustrates in detail operations performed to obtain weight values applied to N pieces of projection data, according to an embodiment of the present disclosure.

FIG. 10 illustrates in detail operations performed to obtain weight values applied to N pieces of projection data, according to an embodiment of the present disclosure. In FIG. 10, the same components as those in FIG. 9A are represented by the same reference numerals. Thus, descriptions that are already provided above with respect to FIG. 9A will be omitted here.

Referring to FIG. 10, N pieces of projection data respectively corresponding to N views included in a first angular range are acquired (S910). The memory 310 then stores the N pieces of projection data respectively corresponding to the N views included in the first angular range. Furthermore, the N pieces of projection data may be data acquired by removing noise from initially acquired raw data. For example, the N pieces of projection data respectively corresponding to the N views may be acquired by smoothing the initially acquired raw data.

The controller 320 back-projects a projection data set, i.e., M pieces of projection data respectively corresponding to M views that are some of the N views, to thereby generate M back-projection images respectively corresponding to the M views (S1010).

In detail, the M pieces of projection data that are a subset for obtaining a final weight map may be selected among the N pieces of projection data. In this case, the M pieces of projection data may be data acquired by removing the noise (e.g. smoothing, etc.).

The M pieces of projection data respectively corresponding to the M views may then be back-projected to generate M back-projection images. Here, the M back-projection mages may be back-projection images respectively corresponding to the M views. Furthermore, each of the M back-projection images may represent a part of the object and include a plurality of voxels.

Subsequently, M first weight maps to be respectively applied to the M back-projection images corresponding to the M views are obtained (S1020). In this case, the M first weight maps are used to respectively correct the M back-projection images. For example, a first weight map corresponding to a first view may be used to correct a first back-projection image corresponding to the first view. In detail, the first weight map corresponding to the first view may be used to correct pixel values in a predetermined region of the first back-projection image corresponding to the first view. Here, 'the predetermined region' may be a region corresponding to a material having a high X-ray attenuation rate compared to its surrounding region.

In detail, a mean value and a standard deviation for voxels in the M back-projection images may be calculated, and then a first weight map applied when each of the M pieces of projection data is back-projected may be obtained based on the calculated mean value and standard deviation.

In detail, a weight value may be obtained by using Equation (1) below. Here, the first weight map is a map for correcting an abnormally high pixel value in each of the M back-projection images. For example, a first weight map may be used to lower an abnormally high pixel value when the abnormally high pixel value appears in a portion where a metallic material is located in a back-projection image. Furthermore, the first weight map may be used to increase a value of a pixel that appears abnormally dark around a metallic material in a back-projection image.

$$W(i_n, j) = \frac{1}{\sigma_j \sqrt{2\pi}} \exp\left(-\frac{1}{2}\left(\frac{I(i_n, j) - \mu_j}{\sigma_j}\right)^2\right) \quad \text{Equation (1)}$$

where $W(i_n, j)$ denotes a weight value applied to a j-th voxel in n-th projection data among the M pieces of projection data, $I(i_n, j)$ denotes a value back-projected onto the j-th voxel from the n-th projection data among the M pieces of projection data, $\mu_j$ denotes a mean value of values back-projected onto j-th voxels from the M pieces of projection data, and $\sigma_j$ denotes a standard deviation of values back-projected onto the j-th voxels from the M pieces of projection data.

Thus, a weight map corresponding to each of the M pieces of projection data may be obtained. In detail, weight values respectively corresponding to voxels included in each of the M pieces of projection data may be obtained by using Equation (1). Furthermore, a collection of weight values respectively applied to voxels included in one projection data may be generated as a 'first weight map'.

As described above, the weight map may consist of weight values respectively applied to a plurality of voxels included in the voxel region 800. Referring to FIGS. 8 and 15A, a final weight map may be generated in such a manner as to increase a pixel value corresponding to at least one voxel in a dark region 1521 in which undershoot artifacts occur. For example, when a pixel value corresponding to a voxel is Pi, a weight value corresponding to the voxel may be represented by Wi. When a pixel value corresponding to a voxel to which a weight value is Pi_correct, the pixel value may be calculated as Pi_correct=Pi*Wi.

Thus, in an embodiment of the present disclosure, an operation of correcting a pixel value in such a manner to reduce or remove metal artifacts may mean an operation of weighting at least one pixel value corresponding to at least one voxel by using a weight map including weight values respectively corresponding to voxels. In detail, the 'weighting operation' may be an operation of correcting a pixel value corresponding to a voxel by multiplying the pixel value corresponding to the voxel by a weight value Wi as described above.

As another example, bone or calcareous material as well as metal may be used as a material imaged with a large pixel value compared to its surrounding region. In other words, when a material having a high X-ray attenuation rate exists in an object, a region corresponding to the material having the high X-ray attenuation rate is captured in a tomography image that is an X-ray image with a large pixel value compared to a surrounding region. When an object including such a material with a high X-ray attenuation rate compared to its surrounding region is imaged, artifacts similar to metal artifacts may occur in a surrounding region where a material with a low X-ray attenuation rate is imaged due to the presence of the material with a high X-ray attenuation rate. Thus, when an object including a material having a high X-ray attenuation rate is imaged, a weight map may include a weight value applied to a predetermined voxel such that artifacts appearing due to the material are alleviated.

As described above, the first weight map may be obtained using the mean and standard deviation of voxel values in the M pieces of projection data.

Subsequently, M first corrected back-projection images to which the first weight maps are applied are generated by respectively applying the M first weight maps corresponding to the M views to the M back-projection images (S1030). For example, when the M pieces of projection data include projection data corresponding to a first view, the first weight map corresponding to the first view, which is applied when the projection data corresponding to the first view is back-projected, may be generated using Equation (1) in operation S1020. Then, a back-projection image corresponding to the first view, which is generated by back-projecting the projection data corresponding to the first view, may be corrected by applying the first weight map corresponding to the first view to the back-projection image corresponding to the first view. Accordingly, a first corrected back-projection image corresponding to the first view may be generated.

As a result, the M first corrected back-projection images respectively corresponding to the M views are generated in operation S1030.

Subsequently, N final weight maps applied when the N pieces of projection data are back-projected may be obtained by using mean values of voxels in the M first corrected back-projection images (S1040).

In detail, the mean values of voxels in the M first corrected back-projection images generated in operation S1030 are calculated. A mean of values of each voxel in the M first corrected back-projection images is set as a 'reference value' for each voxel. For example, a mean of j-th voxel values in the M first corrected back-projection images may be set as a reference value for a j-th voxel.

Then, N back-projection images are generated by respectively back-projecting the N pieces of projection data. In other words, the N back-projection images respectively corresponding to the N views are generated.

By setting a mean value as the reference value, a standard deviation for each voxel in the N back-projection images is calculated. Then, N final weight maps applied when the N pieces of projection data are respectively back-projected are obtained (S1040). In other words, the N final weight maps respectively corresponding to the N views are obtained.

The N final weight maps respectively corresponding to the N views may be calculated by using the above Equation (1).

However, in obtaining a final weight map, variables in Equation (1) may be defined as follows. In Equation (1), $W(i_n,j)$ denotes a weight value applied to a j-th voxel from n-th projection data among the N pieces of projection data. $I(i_n,j)$ denotes a value back-projected onto the j-th voxel from the n-th projection data among the N pieces of projection data, $\mu_j$ may be a reference value for the j-th voxel. $\sigma_j$ denotes a standard deviation of values back-projected onto the j-th voxels from the N pieces of projection data, which is calculated by using a mean value for each voxel in the N pieces of projection data as a reference value.

Accordingly, a final weight map corresponding to each of the N pieces of projection data may be obtained.

FIG. 11 is a flowchart illustrating in detail operations performed to obtain a tomography image, according to an embodiment of the present disclosure. In FIG. 11, the same components as those in FIG. 9B are represented by the same reference numerals. Thus, descriptions that are already provided above with respect to FIGS. 9A through 9B will be omitted here.

Figure 12A:
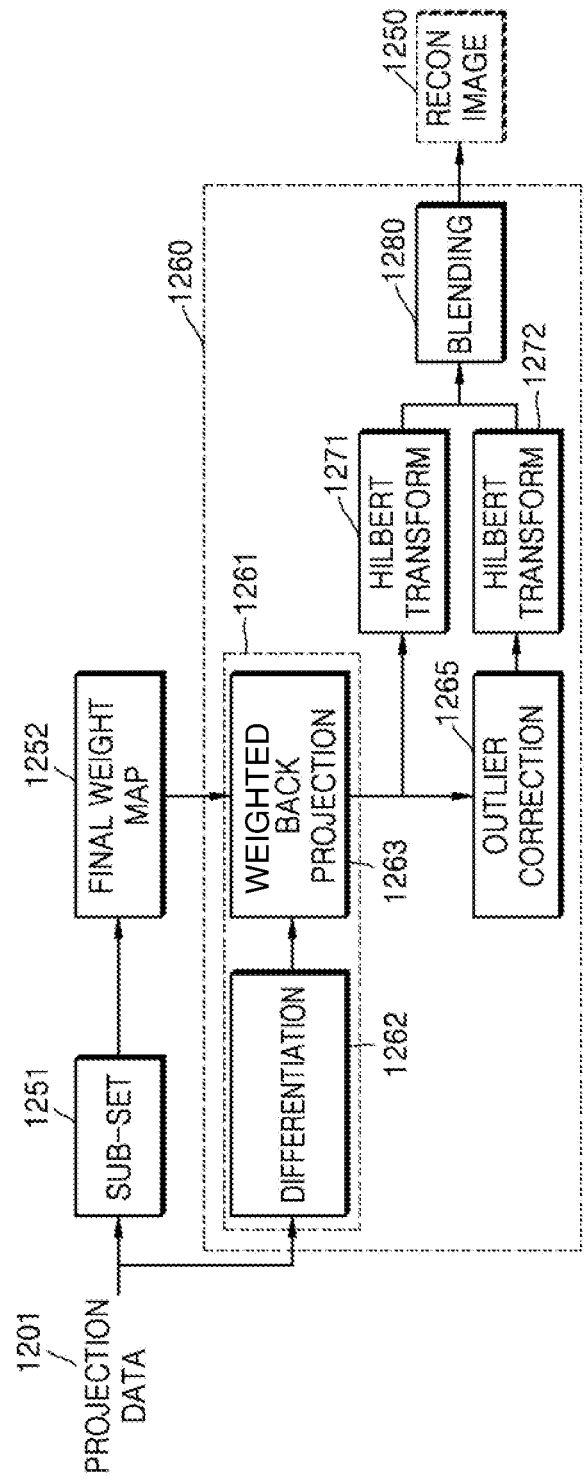
FIG. 12A is a diagram for explaining in detail operations performed to obtain a tomography image, according to an embodiment of the present disclosure.
Figure 12B:
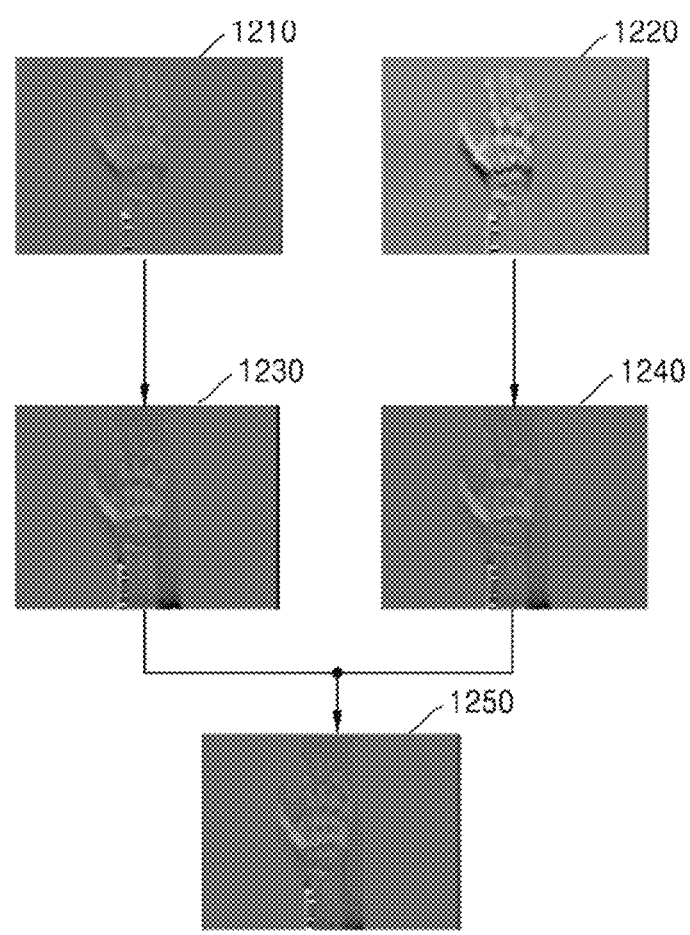
FIG. 12B is another diagram for explaining in detail operations performed to obtain a tomography image, according to an embodiment of the present disclosure.

FIGS. 12A and 12B are other diagrams illustrating in detail operations performed to obtain a tomosynthesis image in an embodiment of the present disclosure.

Referring to FIG. 11, N differentiated images obtained by respectively differentiating the N pieces of projection data are corrected by using the corresponding final weight maps obtained in operation S920. A first differentiated back-projection image is generated by back-projecting the corrected N differentiated images (S930).

In detail, operation S930 may be performed as follows.

The N differentiated images respectively corresponding to N views are generated by respectively differentiating the N pieces of projection data. The N differentiated images are then corrected by applying final weight maps respectively corresponding to the N differentiated images. One first differentiated back-projection image is generated by back-projecting the corrected N differentiated images. In other words, the first differentiated back-projection image may be generated using a back-projection process in which the corrected N differentiated images are accumulated and summed.

Furthermore, operation S940 of FIG. 9B may include operations S1110, S1120, and S1130.

In detail, a first corrected differentiated back-projection image is generated by correcting pixel values of a region corresponding to a predetermined material in the first differentiated back-projection image obtained in operation S950 (S1110). Operation S1110 may be performed by the controller 320.

In operation S1110, pixel values of a region corresponding to a material having a high X-ray attenuation rate compared to its surrounding region are to be corrected. In other words, in operation S1110, the first corrected differentiated back-projection image may be generated by correcting pixel values of a region corresponding to a material having a high X-ray attenuation rate compared to its surrounding region in the first differentiated back-projection image.

Here, 'correction of pixel values' may be performed by adjusting pixel values corresponding to a material having a high X-ray attenuation rate in a direction in which the pixel values are decreased. In detail, the 'correction' in operation S1110 may mean not only setting pixel values corresponding to a predetermined material to 0 but also decreasing the pixel values corresponding to the predetermined material. Furthermore, the 'correction' may be performed by replacing pixel values corresponding to a predetermined material having a high X-ray attenuation rate with pixel values of a region surrounding the predetermined material. In addition, the 'correction' may be performed by replacing pixel values corresponding to a predetermined material having a high X-ray attenuation rate with an average value of pixel values around the predetermined material.

For example, an artificial material such as metal may be the material having a high X-ray attenuation rate compared to its surrounding region. As another example, bone may be the material that has a high X-ray attenuation rate compared to its surrounding region. Bone is surrounded by soft tissue and has a high X-ray attenuation rate compared to the soft tissue. In this case, artifacts similar to metal artifacts may occur in a region where the surrounding soft tissue is imaged due to the bone. Thus, when bone surrounded by soft tissue with a low X-ray attenuation rate is imaged, it is necessary to correct artifacts occurring in the surrounding soft tissue due to the bone. Furthermore, a material calcified in the object may be an example of the material having a high X-ray attenuation rate compared to its surrounding region. When calcification progresses in bone, soft tissue adjacent to the bone, or other soft tissues, a calcareous material generated due to the calcification has a higher X-ray attenuation rate than the surrounding soft tissues.

Furthermore, a 'region with an abnormally large pixel value', such as a region where a metal, bone, or calcified material is imaged, may be referred to as an outlier region'. Furthermore, whether a region is an outlier region may be determined based on whether a pixel value of the region is greater than or equal to or exceeds a threshold value.

Thus, the predetermined material to be removed in operation S1110 may be an artificial material such as the metal, bone, or calcareous material.

The first corrected differentiated back-projection image may be generated by correcting a pixel value that is greater than or equal to or exceeds a threshold value based on pixel values in the first differentiated back-projection image.

In addition, the threshold value may be a mean pixel value of an image (e.g., the first differentiated back-projection image to be corrected), a mean pixel value of a predetermined region in the first differentiated back-projection image, a pixel value corresponding to a metallic material in the first differentiated back-projection image, a pixel value corresponding to a bone in the first differentiated back-projection image, or a pixel value corresponding to a calcareous material in the first differentiated back-projection image. Alternatively, the threshold value may be a value that is greater than or equal to a mean pixel value of the first differentiated back-projection image by a predetermined offset, or a value that is greater than or equal to a mean pixel value of a predetermined region in the first differentiated back-projection image.

Alternatively, the threshold value may be set to an experimentally optimized value based on a quality of a corrected image (e.g., the first corrected differentiated back-projection image or a final tomosynthesis image).

Furthermore, the threshold value may be a maximum pixel value corresponding to a material constituting the body (in particular, a natural material of the body other than an artificial material). In other words, a pixel value that is greater than or equal to or exceeds the threshold value may be determined as a pixel value corresponding to an artificial material captured in an image.

In detail, a differentiated image is an image showing a sharper edge or border of the imaged object. Thus, a differentiated image or a differentiated back-projection image obtained by back-projecting the differentiated image includes information about an edge or border of the object. For example, in a differentiated image or a differentiated back-projection image, a signal value in an edge adjacent to or surrounding a metallic material having a large attenuation coefficient is greater than a signal value in a non-metallic region. Thus, in the differentiated image or differentiated back-projection image, a pixel value in a region corresponding to a metallic material in the differentiated image or differentiated back-projection image may be corrected by using a thresholding method in which a signal value larger than a predetermined threshold value may be corrected.

Accordingly, the first corrected differentiated back-projection image is generated by correcting a pixel value of a region corresponding to a material with a high X-ray attenuation rate, such as metal, included in the first differentiated back-projection image. In other words, a first corrected differentiated back-projection image (1220 in FIG. 12B) may be generated by correcting a pixel value of a region corresponding to a material having a high X-ray attenuation rate in the first differentiated back-projection image (1210 in FIG. 12B) (e.g., correction such as decreasing the pixel value of the region to a mean pixel value). Here, correction of a pixel value corresponding to a material having a high X-ray attenuation rate, such as metal, which is captured in the first differentiated back-projection image 1210, may be referred to as 'outlier correction'.

Hereinafter, detailed operations for generating a final tomosynthesis image described with reference to FIG. 11 will be described in more detail with reference to FIGS. 12A and 12B.

FIG. 12A is a diagram for explaining in detail operations performed to obtain a tomography image, according to an embodiment of the present disclosure.

Referring to FIG. 12A, M pieces of projection data 1251 respectively corresponding to M views are selected from among N pieces of projection data 1201 respectively corresponding to N views included in a first angular range. Final weight maps 1252 are then obtained as described with reference to operation S920.

Subsequently, N edge images respectively representing edge information in the N pieces of projection data are corrected using the corresponding final weight maps and then back-projected to generate a first image. In detail, the N edge images may be N differentiated images. In other words, the first differentiated back-projection image 1210 may be generated by performing weighted back-projection on the N differentiated images obtained by differentiating (1262) the N pieces of projection data 1201, i.e., by applying the final weight maps to the N differentiated images before back-projection.

Subsequently, as described in operation S1110, the first corrected differentiated back-projection image 1220 may be obtained by performing outlier correction 1265 for correcting a pixel value of a region corresponding to a material with a high X-ray attenuation rate, such as metal, included in the first differentiated back-projection image 1210.

FIG. 12B is another diagram for explaining in detail operations performed to obtain a tomography image, according to an embodiment of the present disclosure. In FIG. 12B, the same components as those in FIG. 12A are represented by the same reference numerals.

In an embodiment of the present disclosure, the controller 320 may generate a final tomosynthesis image by using the first differentiated back-projection image 1210 and the first corrected differentiated back-projection image 1220.

In detail, Hilbert transform 1271 is performed on the first differentiated back-projection image 1210, and Hilbert transform 1272 is performed on the first corrected differentiated back-projection image 1220 (S1120).

A final tomosynthesis image 1250 is generated by blending (1280) a Hilbert-transformed first differentiated back-projection image 1230 with a Hilbert-transformed first corrected differentiated back-projection image 1240.

Here, the blending operation may be performed in various ways. The blending operation may mean an operation of generating one image by mixing, combining, or using at least two images together. For example, the final tomosynthesis image 1250 may be generated by selectively capturing whichever one of the Hilbert-transformed first differentiated back-projection image 1230 and the Hilbert-transformed first corrected differentiated back-projection image 1240 has larger pixel values.

As another example, the final tomosynthesis image 1250 may be generated by averaging the Hilbert-transformed first differentiated back-projection image 1230 and the Hilbert-transformed first corrected differentiated back-projection image 1240.

As another example, the final tomosynthesis image 1250 may be generated by performing a root mean square (RMS) operation on the Hilbert-transformed first differentiated back-projection image 1230 and the Hilbert-transformed first corrected differentiated back-projection image 1240.

In addition, various techniques for blending two images may be used.

In another method of reconstructing a tomography image, a tomography image is generated by performing FBP on N pieces of projection data, i.e., by filtering the N pieces of projection data and then back-projecting them, as in the second reconstruction method described above. A tomography image generation method 1300 according to another embodiment of the present disclosure based on the second reconstruction method and detailed operations of the X-ray imaging apparatus 300 according to the tomography image generation method 1300 will now be described in detail with reference to FIGS. 13 and 14.

FIG. 13 is a flowchart of a tomography image generation method, according to another embodiment of the present disclosure. In FIG. 13, the same components as those in FIGS. 9A through 11 are represented by the same reference numerals. Thus, descriptions that are already provided above with respect to FIGS. 9A through 11 will be omitted when describing the embodiment illustrated in FIG. 13.

Figure 14:
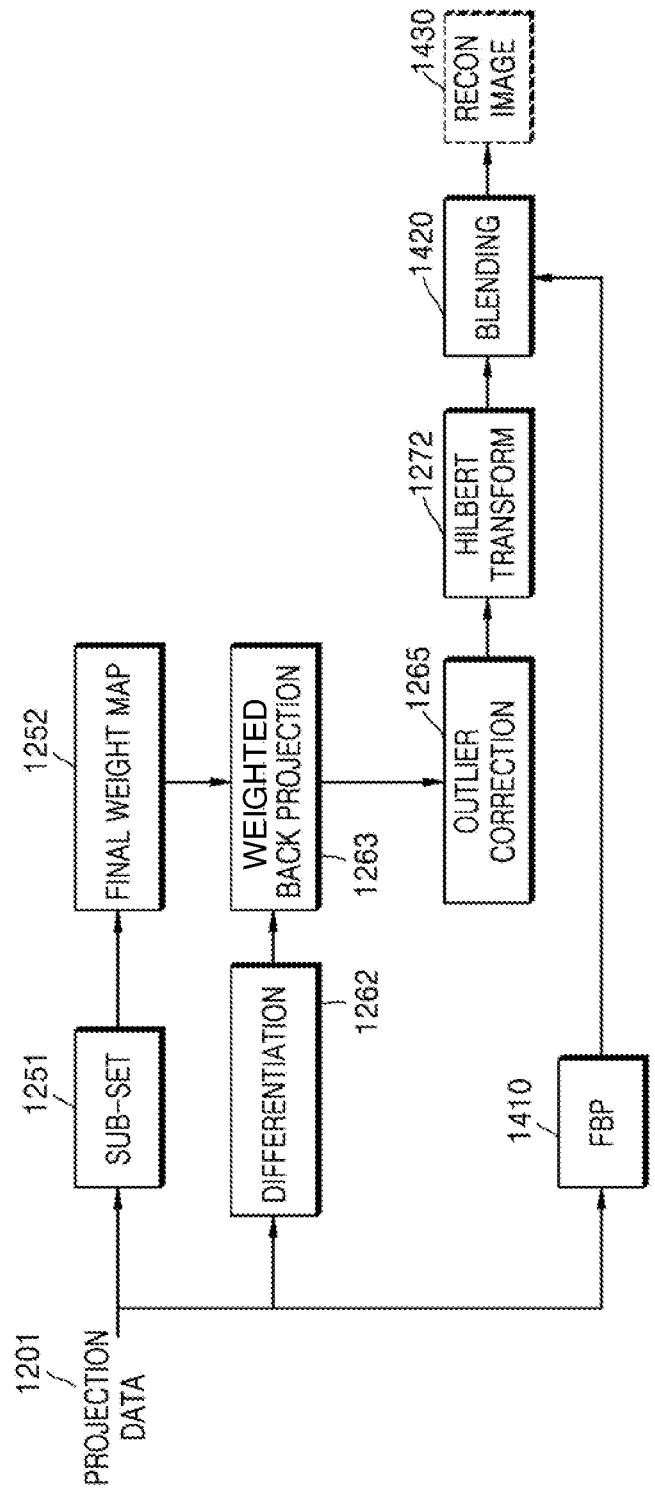
FIG. 14 is a diagram for explaining in detail operations performed to obtain a tomography image, according to another embodiment of the present disclosure.

FIG. 14 is a diagram for explaining in detail operations performed to obtain a tomography image, according to another embodiment of the present disclosure. In FIG. 14, the same components as those in FIG. 12A are represented by the same reference numerals. Thus, descriptions that are already provided above with respect to FIG. 12A will be omitted when describing the embodiment illustrated in FIG. 14.

Referring to FIGS. 13 and 14, in the tomography image generation method according to the other embodiment of the present disclosure, N pieces of projection data (a projection data set) respectively corresponding to N views included in a first angular range are acquired (S910). The X-ray imaging apparatus 300 may acquire the N pieces of projection data respectively corresponding to the N views included in the first angular range and store the N pieces of projection data in the memory 310. In detail, the N pieces of projection data may be stored in the memory 310 according to control by the controller 320.

Then, the final weight maps 1252 applied to the N pieces of projection data are obtained based on the M pieces of projection data 1251 respectively corresponding to the M views that are some of the N views (S920). In detail, final weight maps applied when the N pieces of projection data are back-projected may be obtained based on the M pieces of projection data respectively corresponding to the M views among the N views. The operation of operation S920 may be performed by the controller 320.

Subsequently, N edge images respectively representing edge information in the N pieces of projection data may be corrected using the final weight maps 1252 obtained in operation S910 and then back-projected to generate a first image (S950). Operation S950 may be performed by the controller 320. In this case, the first image may be above-described first differentiated back-projection image.

A first corrected image (e.g., a first differentiated back-projection image) is generated by correcting pixel values of a region corresponding to a predetermined material in the first differentiated back-projection image obtained in operation S950 (S1110). The material to be corrected in operation S1110 may be a material having a higher X-ray attenuation rate compared to its surrounding region. Operation S1110 may be performed by the controller 320.

Then, frequency modulation transformation may be performed on the first corrected image (e.g., the first corrected differentiated back-projection image) obtained in operation S1110 to generate a frequency modulation-transformed first corrected image. In detail, the Hilbert transform 1272 may be performed on the first corrected image (e.g., the first corrected differentiated back-projection image) obtained in operation S1110 to generate a Hilbert-transformed first corrected differentiated back-projection image (S1310). Operation S1310 may be performed by the controller 320.

Furthermore, in the tomography image generation method 1300, FBP 1410 may be performed on the N pieces of projection data to generate an FBP image (S1320). Operation S1320 may be performed by the controller 320. In this case, the FBP image generated in operation S1320 may correspond to an image obtained by performing the Hilbert transform 1271 on the first differentiated back-projection image 1210 described with reference to FIG. 12B.

Then, according to the tomography image generation method 1300, a final tomography image 1430 may be generated by blending (1420) the frequency modulation-transformed first corrected image (e.g., the Hilbert-transformed first corrected differentiated back-projection image) with the FBP image obtained in operation S1320 (S1330). Operation S1330 may be performed by the controller 320.

FIG. 15A illustrates a tomosynthesis image obtained according to a conventional tomography image generation method In the related art, various techniques are used to reduce artifacts such as ripple artifacts and/or undershoot artifacts that occur during generation of an X-ray image such as a tomosynthesis image due to a material having a high X-ray attenuation rate, e.g., an artificial material such as a metallic material, bone, and/or a calcareous material.

A representative technique involves calculating weight values by using mean values for all pieces of projection data used to obtain a tomosynthesis image and correcting image values of an abnormal point or abnormal region by using the obtained weight values to generate a tomosynthesis image. In detail, when weight values are calculated using a mean value for all pieces of projection data corresponding to all views included in a predetermined angular range, an afterimage of a metallic material is not properly removed, and thus, artifacts caused by the metallic material are not effectively removed.

Figure 15B:
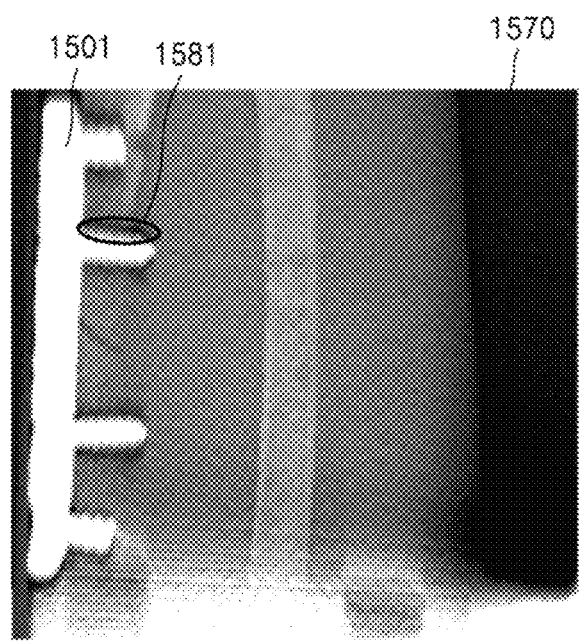
FIG. 15B illustrates a tomography image obtained according to an embodiment of the present disclosure.

An example in which metal pins are inserted into an object as a metallic material having a high X-ray attenuation rate is illustrated in FIGS. 15A and 15B and will now be described with reference thereto.

When a metal pin 1501 is embedded in a bone 1502, FIG. 15A illustrates a tomosynthesis image 1510 generated by removing artifacts according to the related art.

In the tomosynthesis image 1510, due to ripple artifacts caused by the metal pin 1501 that is a metallic material, a region including the metal pin 1501 is imaged with extremely high pixel values, and an afterimage remains in an outlier region 1521 that is the region including the metal pin 1501 such that the outlier region 1521 appears too dark.

Accordingly, the tomosynthesis image 1510 appears entirely distorted, and thus, efficiency and accuracy of image analysis by a user such as a doctor may be degraded.

FIG. 15B illustrates a tomosynthesis image obtained according to an embodiment of the present disclosure.

FIG. 15B shows a final tomosynthesis image 1570 generated in an embodiment of the present disclosure.

As described above, according to techniques of the related art, all pieces of projection data obtained at all angles are used to calculate a reference value or weight value for finding and correcting an abnormal point or an abnormal region at which a material such as a metallic material is imaged. In detail, mean values for all pieces of projection data obtained from all angles are used when calculating the reference value or weight for the above-described correction, In the case of using mean values for all pieces of projection data at all angles, when X-rays encounter a matter having a large attenuation coefficient (e.g., a metallic material) as they pass through a plurality of X-ray paths corresponding to a plurality of views in a region where an afterimage of a metallic material appears, a mean value of values back-projected onto a voxel is greatly affected by pixel values in a region having a large attenuation coefficient. Thus, it is difficult to reduce artifacts only by calculating a mean and standard deviation.

In this case, when several pieces of projection data (e.g., M pieces of projection data) are selected instead of all pieces of projection data (e.g., N pieces of projection data) acquired over the entire angular range and then the selected several pieces of projection data (e.g., M pieces of projection data) are back-projected, the number of X-ray paths passing through a matter having a large attenuation coefficient is relatively reduced. In other words, in the case of using pieces of data acquired to calculate a reference value or a weight value according to the related art, the number of paths of X-rays passing through a material having a large attenuation coefficient, such as a metal pin, is N. In the present disclosure in which the M pieces of projection data are acquired to calculate weight values, the number of X-ray paths is M. Here, M is an integer less than or equal to N. Thus, when a weight value is obtained using some pieces of projection data, a size of a region in which an afterimage of a matter having a large attenuation coefficient is formed is also reduced.

Accordingly, when pieces of projection data to be back-projected are corrected using a weight map obtained according to an embodiment of the present disclosure, a size of a region where artifacts caused by a material having a large attenuation coefficient, such as ripple artifacts, occur is further reduced.

Furthermore, in the related art, when a large metal is inserted into an object, since a number of X-ray paths pass through the metal, a strong afterimage appears even at a depth far from the metal. On the other hand, in an embodiment of the present disclosure, even in such a case, because pieces of projection data corresponding to several views (e.g., M pieces of projection data) are used to obtain weight values, the number of paths of X-rays passing through the metal may be reduced, and accordingly, a strength of an afterimage may be effectively diminished.

Furthermore, according to an embodiment of the present disclosure, distortion of an image caused by a material having a high X-ray attenuation rate may be effectively reduced via the above-described outlier correction.

Referring to FIG. 15B, as seen in the final tomosynthesis image 1570 generated according to the embodiment of the present disclosure, a size of a region 1581 in which an afterimage appears around the metal pin 1501 is significantly reduced compared to that in the tomosynthesis image 1510 shown in FIG. 15A.

A tomosynthesis image generation method according to an embodiment of the disclosure may be implemented through computer-readable recording media having stored thereon computer-executable instructions and data. The instructions may be stored in the form of program code, and when executed by a processor, generate a predefined program module to perform a predetermined operation. Furthermore, when executed by the processor, the instructions may perform a plurality of operations included in the tomosynthesis image generation method according to the embodiment of the disclosure.

Furthermore, embodiments of the disclosure may be implemented as a software program including instructions stored in computer-readable storage media.

A computer may refer to a device configured to retrieve an instruction from a computer-readable storage medium and to operate in response to the retrieved instruction according to embodiments of the disclosure and may include a CT system according to embodiments of the disclosure.

The computer-readable storage medium may be provided in the form of a non-transitory storage medium. In this regard, the term 'non-transitory' only means that the storage medium does not include a signal and is tangible, and the term does not distinguish between data that is semi-permanently stored and data that is temporarily stored in the storage medium.

In addition, tomosynthesis image generation methods according to embodiments of the disclosure may be included in a computer program product when provided. The computer program product may be traded, as a product, between a seller and a buyer. The computer program product may include a software program and a computer-readable storage medium having stored thereon the software program. For example, the computer program product may include a product (e.g., a downloadable application) in the form of a software program electronically distributed by a manufacturer of the CT system or through an electronic market (e.g., Google™, Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., a CT system), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In this case, one of the server, the terminal, and the third device may execute the computer program product to perform methods according to embodiments of the disclosure. Alternatively, at least two of the server, the terminal, and the third device may execute the computer program product to perform the methods according to the embodiments of the disclosure in a distributed manner.

For example, the server (e.g., a cloud server, an artificial intelligence server, or the like) may execute the computer program product stored in the server to control the terminal communicating with the server to perform the tomosynthesis image generation methods according to the embodiments of the disclosure.

As another example, the third device may execute the computer program product to control the terminal communicating with the third device to perform the tomosynthesis image generation methods according to the embodiments of the disclosure. As a specific example, the third device may remotely control an X-ray apparatus or CT system to emit X-rays toward an object and generate a final tomography image according to an embodiment of the present disclosure, which is an image of an internal part of the object, based on information about radiation detected by the an X-ray detector as it passes through the object.

The disclosed embodiments have been described above with reference to the accompanying drawings. It will be understood by those of ordinary skill in the art that various changes in form and details may be made therein without departing from essential characteristics or the spirit and scope of the disclosure as defined by the appended claims. The disclosed embodiments are examples only and are not to be construed for purposes of limitation.

The invention claimed is:

1. A method of generating a tomography image, the method comprising:
acquiring N pieces of projection data respectively corresponding to N views included in a first angular range;
obtaining, based on M pieces of projection data respectively corresponding to M views among the N views, a final weight map applied when the N pieces of projection data are back-projected; and
generating a final tomography image showing an object by using the final weight map and the N pieces of projection data;
wherein the final weight map is configured to remove or reduce ripple artifacts and undershoot artifacts due to a presence of afterimage data in the projection data that corresponds to a presence of metallic material.

2. The method of claim 1, wherein the M views are views extracted at a predetermined interval from among the N views included in the first angular range, and M has a value less than or equal to N.

3. The method of claim 2, wherein the predetermined interval is an equal angular interval.

4. The method of claim 1, further comprising generating a first image by correcting, based on the final weight map, N edge images respectively representing edge information in the N pieces of projection data and then back-projecting the corrected N edge images,
wherein the generating of the final tomography image comprises generating the final tomography image by using the first image.

5. The method of claim 4, wherein the generating of the final tomography image comprises:
generating a first corrected image by correcting a pixel value of a region corresponding to a material having a high X-ray attenuation rate compared to its surrounding region included in the first image; and
generating the final tomography image by using the first image and the first corrected image.

6. The method of claim 5, wherein the material having a high X-ray attenuation rate compared to the surrounding region is at least one of a material made of metal inserted into a human body, bone, or a calcareous material.

7. The method of claim 5, wherein the generating of the first corrected image comprises generating a first corrected differentiated back-projection image by correcting, based on a pixel value of the first image, a pixel value of an outlier region in which the pixel value is greater than or equal to a predetermined threshold value or exceeds the predetermined threshold value.

8. The method of claim 4, wherein the generating of the first image comprises generating a first differentiated back-projection image that is the first image by correcting, based on the final weight map, N differentiated images obtained by respectively differentiating the N pieces of projection data and then back-projecting the corrected N differentiated images.

9. The method of claim 4, wherein the generating of the final tomography image comprises:
generating a first corrected image by correcting a pixel value of a region corresponding to a material having a high X-ray attenuation rate compared to its surrounding region included in the first image; and
generating the final tomography image by performing frequency modulation transformations respectively on the first image and the first corrected image and blending a frequency modulation-transformed first image with a frequency modulation-transformed first corrected image.

10. The method of claim 1, wherein the acquiring of the N pieces of projection data comprises acquiring the N pieces of projection data via X-ray imaging in an X-ray apparatus by emitting X-rays toward the object while moving an X-ray radiation device over the first angular range and detecting X-rays that have passed through the object.

11. The method of claim 1, wherein the acquiring of the N pieces of projection data comprises acquiring the N pieces of tomography data from a computed tomography (CT) system or a tomosynthesis system.

12. The method of claim 1, further comprising:
generating a first image by correcting, based on the final weight map, N edge images generated by respectively performing edge enhancement for edge information in the N pieces of projection data and then back-projecting the corrected N edge images;

generating a first corrected image by correcting a pixel value of a region corresponding to a material having a high X-ray attenuation rate compared to its surrounding region included in the first image;

generating a frequency modulation-transformed first corrected image by performing frequency modulation transformation on the first corrected image; and generating a filtered back-projection image by performing filtered back-projection on the N pieces of projection data, wherein the generating of the final tomography image comprises generating the final tomography image by blending the frequency modulation-transformed first corrected image with the filtered back-projection image.

13. A method of generating a tomography image, the method comprising:

acquiring N pieces of projection data respectively corresponding to N views included in a first angular range;

obtaining, based on M pieces of projection data respectively corresponding to M views among the N views, a final weight map applied when the N pieces of projection data are back-projected; and generating a final tomography image showing an object by using the final weight map and the N pieces of projection data;

generating a first image by correcting, based on the final weight map, N edge images respectively representing edge information in the N pieces of projection data and then back-projecting the corrected N edge images, wherein the generating of the final tomography image comprises generating the final tomography image by using the first image, wherein the generating of the final tomography image comprises:

generating a first corrected image by correcting a pixel value of a region corresponding to a material having a high X-ray attenuation rate compared to its surrounding region included in the first image; and generating the final tomography image by performing frequency modulation transformations respectively on the first image and the first corrected image and blending a frequency modulation-transformed first image with a frequency modulation-transformed first corrected image, wherein the frequency modulation transformation is Hilbert transform, and wherein the blending comprises selectively capturing one of the Hilbert-transformed first image and the Hilbert-transformed first corrected image having larger pixel values.

14. An X-ray imaging apparatus comprising:

a memory storing N pieces of projection data respectively corresponding to N views included in a first angular range; and a controller storing one or more instructions and including at least one processor configured to perform the stored one or more instructions to:

obtain, based on M pieces of projection data respectively corresponding to M views among the N views, a final weight map applied when the N pieces of projection data are back-projected; and generate a final tomography image showing an object by using the final weight map and the N pieces of projection data;

wherein the final weight map is configured to remove or reduce ripple artifacts and undershoot artifacts due to a presence of afterimage data in the projection data that corresponds to a presence of metallic material.

15. A method of generating a tomography image, the method comprising:

acquiring N pieces of projection data respectively corresponding to N views included in a first angular range;

generating a first image by back-projecting N edge images respectively representing edge information in the N pieces of projection data;

generating a first corrected image by correcting a pixel value of a region corresponding to a material having a high X-ray attenuation rate compared to its surrounding region included in the first image for the first angular range;

generating a frequency modulation-transformed first corrected image by performing frequency modulation transformation on the first corrected image for the first angular range;

generating a filtered back-projection image by performing filtered back-projection on the N pieces of projection data for the first angular range; and generating a final tomography image for the first angular range by blending the frequency modulation-transformed first corrected image with the filtered back-projection image for the first angular range.

16. The method of claim 15:

wherein the frequency modulation transformation is Hilbert transform, and wherein the blending comprises selectively capturing one of the Hilbert-transformed first image and the Hilbert-transformed first corrected image having larger pixel values.

* * * * *